US009040735B2

(12) United States Patent
Aki et al.

(10) Patent No.: US 9,040,735 B2
(45) Date of Patent: May 26, 2015

(54) PROCESS FOR MAKING NITRILES

(71) Applicant: INVISTA NORTH AMERICA S.A.R.L., Wilmington, DE (US)

(72) Inventors: Sudhir Aki, Houston, TX (US); Wyatte E. Allen, Orange, TX (US); Mark Anstrom, Beaumont, TX (US); Charles Nelson Campbell, II, Beaumont, TX (US); Tseng Chao, Beaumont, TX (US); James E. McIntosh, Beaumont, TX (US); Larry E. Moerbe, Orange, TX (US); Bruce Edwin Murphree, Beaumont, TX (US); Mark D. Rogers, Port Arthur, TX (US); William J. Tenn, III, Beaumont, TX (US); Thomas E. Vos, Beaumont, TX (US); Michael W. Wensing, Baytown, TX (US)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

(21) Appl. No.: 14/346,882

(22) PCT Filed: Oct. 4, 2012

(86) PCT No.: PCT/US2012/058668
§ 371 (c)(1),
(2) Date: Mar. 24, 2014

(87) PCT Pub. No.: WO2013/052610
PCT Pub. Date: Apr. 11, 2013

(65) Prior Publication Data
US 2014/0235887 A1    Aug. 21, 2014

Related U.S. Application Data

(60) Provisional application No. 61/544,492, filed on Oct. 7, 2011, provisional application No. 61/577,835, filed on Dec. 20, 2011.

(51) Int. Cl.
C07C 253/00 (2006.01)
C07C 253/08 (2006.01)
C07C 253/18 (2006.01)
C07C 253/10 (2006.01)

(52) U.S. Cl.
CPC ............. *C07C 253/18* (2013.01); *C07C 253/10* (2013.01)

(58) Field of Classification Search
USPC ........................................................ 558/338
See application file for complete search history.

(56) References Cited

U.S. PATENT DOCUMENTS

| 3,496,215 | A | 2/1970 | Drinkard, Jr. et al. |
| 3,496,217 | A | 2/1970 | Drinkard, Jr. et al. |
| 3,536,748 | A | 10/1970 | Drinkard, Jr. et al. |
| 3,655,723 | A | 4/1971 | Drinkard, Jr. et al. |
| 3,631,191 | A | 12/1971 | Kane et al. |
| 3,766,237 | A | 10/1973 | Chia et al. |
| 3,852,329 | A | 12/1974 | Tomlinson |
| 3,903,120 | A | 9/1975 | Shook, Jr. et al. |
| 4,385,007 | A | 5/1983 | Shook, Jr. |
| 4,416,825 | A | 11/1983 | Ostermaier |
| 4,874,884 | A | 10/1989 | McKinney et al. |
| 5,512,696 | A | 4/1996 | Kreutzer et al. |
| 5,688,986 | A | 11/1997 | Tam et al. |
| 5,821,378 | A | 10/1998 | Foo et al. |
| 5,847,191 | A | 12/1998 | Bunel et al. |
| 5,959,135 | A | 9/1999 | Garner et al. |
| 5,981,772 | A | 11/1999 | Foo et al. |
| 6,020,516 | A | 2/2000 | Foo et al. |
| 6,127,567 | A | 10/2000 | Garner et al. |
| 6,812,352 | B2 | 11/2004 | Kreutzer et al. |
| 6,893,996 | B2 | 5/2005 | Chu et al. |
| 2004/0176622 | A1 | 9/2004 | Bartsch et al. |
| 2007/0155978 | A1 | 7/2007 | Jungkamp et al. |
| 2009/0182164 | A1 | 7/2009 | Foo et al. |

FOREIGN PATENT DOCUMENTS

| GB | 2106517 A | 4/1983 |
| WO | 9633969 A1 | 10/1996 |
| WO | 2008028843 A1 | 3/2008 |
| WO | 2011075494 A1 | 6/2011 |
| WO | 2011075496 A1 | 6/2011 |
| WO | 2012033556 A1 | 3/2012 |

OTHER PUBLICATIONS

Baharlou, Simin, International Preliminary Report on Patentability dated Apr. 8, 2014, for International Application No. PCT/US2012/058668, 8 pages.
Dunet, Guillaume, International Search Report dated Jan. 31, 2013, for International Application No. PCT/US2012/058668, 3 pages.

*Primary Examiner* — Samantha Shterengarts
(74) *Attorney, Agent, or Firm* — Robert B. Furr, Jr.

(57) ABSTRACT

The present invention relates to a process for hydrocyanating 3-pentene⁻nitrile. The process can include feeding 3-pentenenitrile and HCN to a hydrocyanation reaction zone that includes a Lewis acid promoter, nickel, and a phosphorus-containing ligand. In various embodiments, the process can also include controlling water concentration within the hydrocyanation reaction zone sufficient to maintain a high activity of the ligand catalyst complex while recycling at least a portion of the ligand catalyst complex.

15 Claims, 3 Drawing Sheets

PROCESS FOR MAKING NITRILES

FIELD OF THE INVENTION

This disclosure relates to a process for manufacturing nitriles. More particularly, the disclosure relates to an improved process for hydrocyanating pentenenitriles to make adiponitrile.

BACKGROUND OF THE INVENTION

Adiponitrile (ADN) is a commercially important and versatile intermediate in the industrial production of nylon polyamides useful in forming films, fibers, and molded articles. ADN can be produced by hydrocyanation of 1,3-butadiene (BD) in the presence of transition metal complexes including various phosphorus-containing ligands. For example, catalysts including nickel and monodentate phosphorus-containing ligands are well documented in the prior art; see, for example, U.S. Pat. Nos. 3,496,215; 3,631,191; 3,655,723 and 3,766,237; and Tolman, C. A., McKinney, R. J., Seidel, W. C., Druliner, J. D., and Stevens, W. R., Advances in Catalysis, 1985, Vol. 33, pages 1-46. Improvements in the hydrocyanation of ethylenically unsaturated compounds with catalysts including nickel and certain multidentate phosphite ligands are also disclosed; e.g., see: U.S. Pat. Nos. 5,512,696; 5,821,378; 5,959,135; 5,981,772; 6,020,516; 6,127,567; and 6,812,352.

3-Pentenenitrile (3PN) can be formed through a series of reactions as illustrated below.

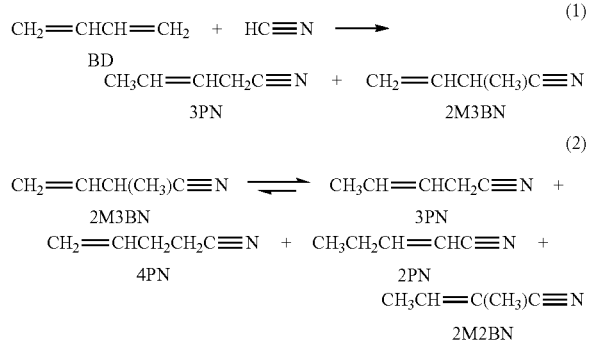

According to abbreviations used herein, BD is 1,3-butadiene, HC≡N is hydrogen cyanide, and 2M3BN is 2-methyl-3-butenenitrile. A method to increase the chemical yield of 3PN from BD hydrocyanation includes the catalytic isomerization of 2M3BN to 3PN (Equation 2 above) in the presence of $NiL_4$ complexes as disclosed in U.S. Pat. No. 3,536,748. Co-products of BD hydrocyanation and 2M3BN isomerization can include 4-pentenenitrile (4PN), 2-pentenenitrile (2PN), 2-methyl-2-butenenitrile (2M2BN), and 2-methylglutaronitrile (MGN).

In the presence of transition metal complexes including various phosphorus-containing ligands, dinitriles such as ADN, MGN, and ethylsuccinonitrile (ESN) can be formed by the hydrocyanation of 3PN and 2M3BN, as illustrated in Equations 3 and 4 below. Equation 4 also shows that 2M2BN can be formed when 2M3BN undesirably isomerizes in the presence of a Lewis acid promoter that can be carried over from a pentenenitrile hydrocyanation reaction zone. Equation 5 shows that 2M2BN can be formed when 2M3BN undesirably isomerizes.

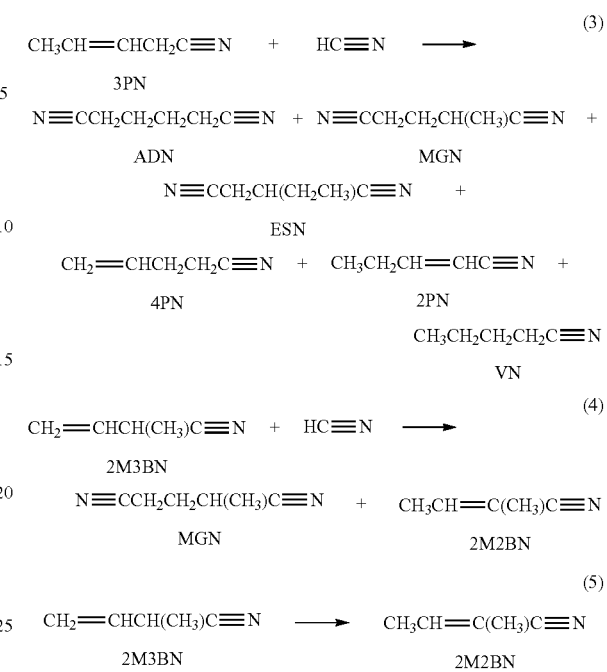

The hydrocyanation of activated olefins such as conjugated olefins (e.g., 1,3-butadiene) can proceed at useful rates without the use of a Lewis acid promoter. However, the hydrocyanation of un-activated olefins, such as 3PN, require at least one Lewis acid promoter to obtain industrially useful rates and yields for the production of linear nitriles, such as ADN. For example, U.S. Pat. Nos. 3,496,217, 4,874,884, and 5,688,986 disclose the use of Lewis acid promoters for the hydrocyanation of non-conjugated ethylenically unsaturated compounds with nickel catalysts including phosphorus-containing ligands.

SUMMARY OF THE INVENTION

Various embodiments of the present invention provide a process for hydrocyanating 3-pentenenitrile. The process includes feeding 3-pentenenitrile and HCN to a hydrocyanation reaction zone including a Lewis acid promoter, nickel and a phosphorus-containing ligand. The process also includes controlling a water concentration within the hydrocyanation reaction zone to be between a detectable level of water and the solubility limit of the mixture within the reaction zone.

Preferably, the ligand is a bidentate phosphorus-containing ligand having the chemical structure of Structure II,

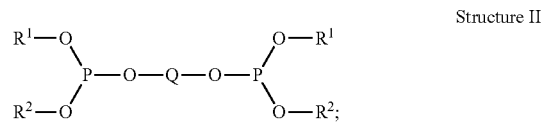

Structure II

In Structure II, O-Q-O is a divalent species of a bisaryl compound selected from the group consisting of Structure III, IV, or V,

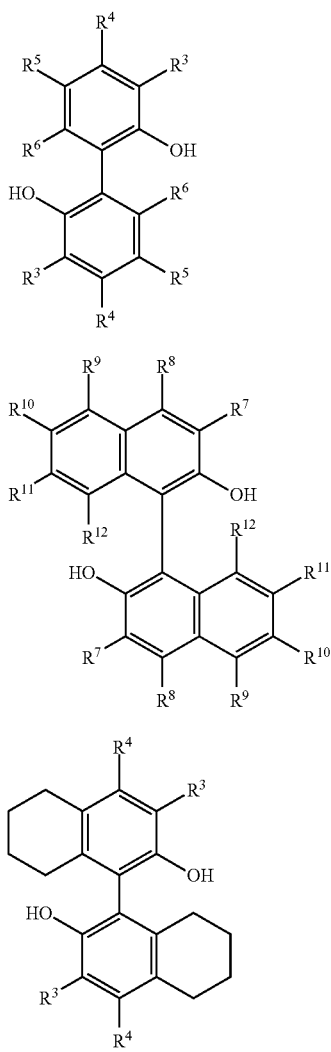

Structure III

Structure IV

Structure V

In Structures II-V, $R^1$ and $R^2$ are the same or different, substituted or unsubstituted, monovalent aryl groups. Also, each of $R^3$, $R^4$, $R^5$, $R^6$, $R^7$, $R^8$, $R^9$, $R^{10}$, $R^{11}$ and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups. The process may also include adding water. Water may be added at any suitable point in the process. For example, water can be added to the hydrocyanation reaction zone. Water can be added to the hydrocyanation reaction zone sufficient to suppress conversion of the bidentate phosphorus-containing ligand to a phosphorus-containing species that forms a ligand-metal complex less catalytically active with respect to pentenenitrile hydrocyanation than a catalyst formed from the phosphorus-containing ligand in the reactor feed. The process may include removing water. Water may be removed at any suitable point in the process. For example, water can be removed from a reaction zone effluent. Sufficient water can be removed from a reaction zone effluent of the hydrocyanation reaction zone to suppress hydrolysis of the bidentate phosphorus-containing ligand in processing downstream of the hydrocyanation reaction zone.

The disclosed process includes controlling the amount of water in the reaction zone. The process is suitably operated continuously to recycle the catalyst complex. Thus in one embodiment, the process can include hydrocyanating 3-pentenenitrile in a reaction zone in the presence of a catalyst complex comprising a phosphorus-containing ligand and nickel metal, comprising flowing 3-pentenenitrile, Lewis acid, HCN and a controlled amount of water to the reaction zone; withdrawing reactor effluent comprising hydrocyanation product and catalyst complex from the reaction zone; contacting the reactor effluent with extraction solvent to recover catalyst complex and remove impurities from the catalyst complex; and recycling at least a portion of the recovered catalyst complex to the reaction zone. The process can include controlling the water concentration in the reaction zone to maintain a desired catalyst composition in the circulating catalyst inventory. In one embodiment, the amount of water in the catalyst complex recharged to the reaction zone is controlled to decrease the deactivation of the catalyst complex. For example, the amount of water in the catalyst complex recharged to the reaction zone is controlled to decrease the deactivation of the catalyst complex to less than about 5% compared to the process without said control. The theoretical mechanism underlying the behavior of the water in the disclosed process is not fully understood.

Examples of suitable water concentrations in the reaction zone include 0.5 ppm up to the saturation limit of the reaction mixture, for example 0.5 ppm to about and about 2000 ppm, or about 1 ppm and 1000 ppm, or from about 5 ppm to about 500 ppm, or from about 10 ppm to about 350 ppm, or from about 20 ppm to about 300 ppm, or at about 240 ppm. Preferably the water concentration is about 100 ppm to about 300 ppm.

In one embodiment, the water is added in an amount sufficient to suppress conversion of the bidentate phosphorus-containing ligand to a phosphorus-containing species that forms a metal-ligand complex less catalytically active with respect to pentenenitrile hydrocyanation than a catalyst formed from the phosphorus-containing ligand in the reactor feed. The process can also include removing sufficient water from a reaction zone effluent of the hydrocyanation reaction zone to suppress hydrolysis of the bidentate phosphorus-containing ligand in a processing downstream of the hydrocyanation reaction zone including liquid-liquid extraction of the phosphorus-containing ligand from a dinitrile derived from the 3-pentenenitrile using a hydrocarbon extraction solvent or in a processing downstream of the hydrocyanation reaction zone including distillation. Thus, when the phosphorus-containing ligand is a bidentate ligand of Structure II above, the water concentration in the reaction zone is controlled to be about 5 ppm to about 500 ppm, for example, 10 ppm to 350 ppm, preferably about 100 ppm to 300 ppm. Various embodiments of the present invention have certain advantages over other process used for hydrocyanation of 3-pentenenitrile. Advantageously, by maintaining particular concentrations of water in the reaction mixture as the catalyst is recycled through a catalyst recovery process, the hydrocyanation catalyst inventory maintains its activity through a greater number of recycle cycles than other processes that have water at higher or lower concentrations. This is surprising because it has been generally understood that water causes degradation of the catalyst complex, thus it is generally taught that the concentration of water should be kept as low as possible in the reaction mixture to maximize the activity of the catalyst complex through repeated recycling cycles. Therefore, contrary to the teachings of the prior art, various embodiments of the present process advantageously and surprisingly maintain a range of water concentrations sufficient to suppress conversion of the bidentate phosphorus-containing ligand to a phosphorus-containing species that forms a ligand-metal complex less catalytically active with respect to pentenenitrile hydrocyanation than a catalyst formed from the phosphorus-containing ligand in the reactor feed. Contrary to the teachings of the prior art, various embodiments of the present process advantageously and surprisingly maintain a range of water concentrations within the reaction zone sufficient to improve activity of the catalyst inventory under continuous operation with downstream liquid-liquid extraction and recycle of the catalyst complex. While not to limit the invention by a recitation of theory, one possible explanation consistent with this discovery is that adding water suppresses formation of one or more products derived from the phosphorus-containing ligand or derived from a catalyst formed from the ligand that can cause decreased catalytic activity of a catalyst mixture recycled from a reaction zone effluent of the hydrocyanation reaction zone or decreased catalytic activity of a catalyst mixture formed from a phosphorus-containing ligand mixture recycled from the reaction zone effluent of the hydrocyanation reaction zone with respect to pentenenitrile hydrocyanation as compared to a catalyst formed from the phosphorus-containing ligand in the reactor feed. Contrary to the teachings of the prior art, various embodiments of the present process advantageously and surprisingly maintain a range of water concentrations to improve catalytic activity within the reaction zone. While not to limit the invention by theory, one possible explanation might be that the water serves to minimize a disproportionation reaction of a phosphorus-containing ligand while also minimizing hydrolysis of the phosphorus-containing ligand, sufficient to suppress formation of one or more products derived from the phosphorus-containing ligand or derived from a catalyst formed from the ligand that can cause decreased catalytic activity of a catalyst mixture recycled from a reaction zone effluent of the hydrocyanation reaction zone or decreased catalytic activity of a catalyst mixture formed from a phosphorus-containing ligand mixture recycled from the reaction zone effluent of the hydrocyanation reaction zone with respect to pentenenitrile hydrocyanation as compared to a catalyst formed from the phosphorus-containing ligand in the reactor feed. In some embodiments, water can then advantageously be removed from a reaction zone effluent prior to recycling of the ligand or the catalyst formed from the ligand to suppress formation of hydrolysis products of the ligand or of the catalyst formed from the ligand during processing of the reactor zone effluent. Various embodiments of the present invention provide a more efficient process of hydrocyanating 3-pentenenitrile than other processes, including by making more efficient use of the valuable ligand or catalyst derived from the ligand, including by maintaining the catalytic activity of the ligand or catalyst formed from the ligand at a higher level though successive recycling of the ligand-containing catalyst complex.

Disclosed embodiments include a process for inhibiting the degradation of DLS as described herein in a 3-pentenenitrile hydrocyanation reaction zone in the presence of Lewis acid, 3-pentenenitrile and HCN comprising controlling the concentration of water at a level sufficient to inhibit degradation of DLS to CLS, TLS and LHP (DLS, CLS, TLS and LHP are defined herein.)

Disclosed embodiments further include a process for stabilizing the composition of a bidentate phosphorus ligand catalyst complex circulating through a 3-pentenenitrile hydrocyanation reaction zone in the presence of Lewis acid, 3-pentenenitrile and HCN comprising controlling the concentration of water at a level sufficient to stabilize the composition. Thus, "controlling" the amount of water may comprise the steps of adding and/or removing water at various points in the process, e.g., the recharging or recycling of catalyst to the reaction zone. By controlling the water content one may decrease the deactivation of the catalyst in the particular process, i.e., the particular feed rates, reactors, temperatures, and other parameters. In the above process, deactivation of the catalyst can be determined by establishing disproportionation and hydrolysis deactivation percentages of the catalyst complex for the particular process. The amount of water in the catalyst complex recharged to the reaction zone can then be controlled to decrease the total percentage deactivation percentages established. By controlling the water content in this way one may decrease the deactivation of the catalyst complex to less than about 5%. The decrease in the deactivation of the catalyst complex may be to less than about 5% compared to the process without the above mentioned water control. That is, one may establish or ascertain the disproportionation and hydrolysis deactivation percentages of the catalyst in the particular process, add or remove water in the recycle or charge and thereby decrease the total percentage thus established or ascertained, for example, to less than about 5%.

DETAILED DESCRIPTION OF THE INVENTION

Figure 1:
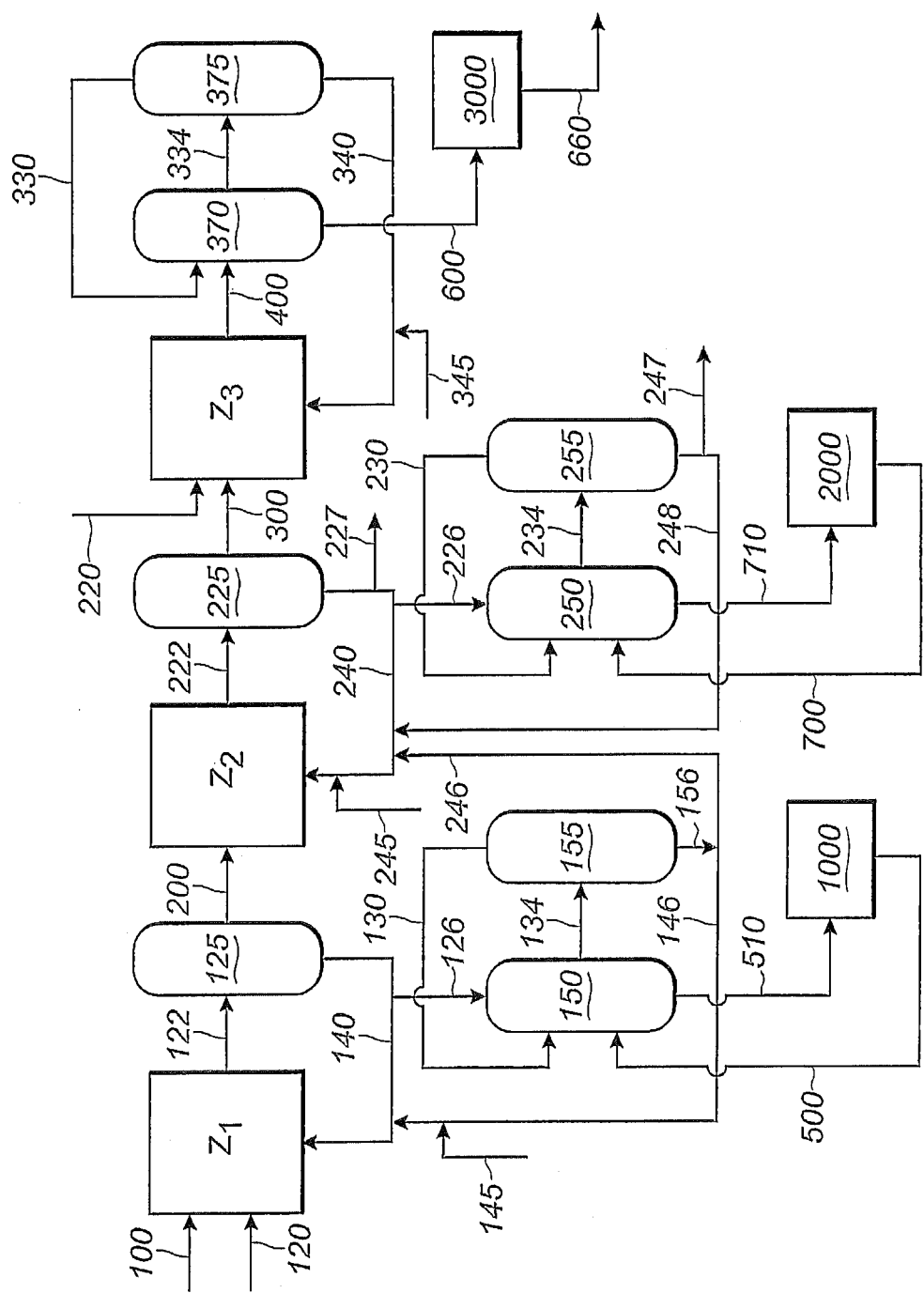
FIG. 1 is a representation of an integrated process for manufacturing 3-pentenenitrile comprising the steps of hydrocyanating 1,3-butadiene, isomerizing 2-methyl-3-pentenenitrile and hydrocyanating 3-pentenenitrile.

Reference will now be made in detail to certain claims of the disclosed subject matter, examples of which are illustrated in the accompanying drawings. While the disclosed subject matter will be described in conjunction with the enumerated claims, it will be understood that they are not intended to limit the disclosed subject matter to those claims. On the contrary, the disclosed subject matter is intended to cover all alternatives, modifications, and equivalents, which can be included within the scope of the presently disclosed subject matter as defined by the claims.

References in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Recitation in a claim to the effect that first a step is performed, then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated, or carried out simultaneously with other steps. In another example, claim elements that recite "Step A, Step B, Step C, Step D, and Step E" can be construed to mean Step A is carried out first, Step B is carried out next, Step C is carried out next, Step D is carried out next, and Step E is carried out last.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

DEFINITIONS

Certain abbreviations and definitions used herein include the following: ADN=adiponitrile; BD=1,3-butadiene; c2PN=cis-2-pentenenitrile; c3PN=cis-3-pentenenitrile; $C_8H_{13}C{\equiv}N$=diolefinic acyclic and monoolefinic cyclic mononitrile compounds of the chemical formula $C_8H_{13}C{\equiv}N$; $C_8H_{14}(C{\equiv}N)_2$=monoolefinic acyclic and aliphatic cyclic dinitrile compounds of the chemical formula $C_8H_{14}(C{\equiv}N)_2$; dinitrile or dinitriles=ADN, MGN, and ESN unless specifically limited; ESN=ethylsuccinonitrile; $HC{\equiv}N$ or HCN=hydrogen cyanide (e.g. hydrocyanic acid); 2M2BN=2-methyl-2-butenenitrile including both (E)-2M2BN and (Z)-2M2BN isomers unless specifically limited; 2M3BN=2-methyl-3-butenenitrile; (E)-2M2BN=(E)-2-methyl-2-butenenitrile; (Z)-2M2BN=(Z)-2-methyl-2-butenenitrile; MGN=2-methylglutaronitrile; organic mononitrile=an organic compound including a single nitrile group, for example, a pentenenitrile; organic dinitrile=an organic compound including two nitrile groups, for example, ADN; pentenenitrile or pentenenitriles=4PN, 3PN, 2PN, 2M3BN, and 2M2BN isomers unless specifically limited; 2PN=2-pentenenitrile including both c2PN and t2PN isomers unless specifically limited; 3PN=3-pentenenitrile including both c3PN and t3PN unless specifically limited; 4PN=4-pentenenitrile; ppm=parts per million by weight unless stated otherwise; ppm=parts per million by weight; t2PN=trans-2-pentenenitrile; t3PN=trans-3-pentenenitrile; VN=valeronitrile; DLS="d-phite" orbidentate phosphorus ligand structure; CLS="c-phite" or phosphorus with bridging phenol ligand structure; TLS="t-phite" or triaryl phosphite ligand structure; LHP=ligand hydrolysis products.

The bidentate phosphorus ligand (DLS) as described above has the chemical structure of Structure A.

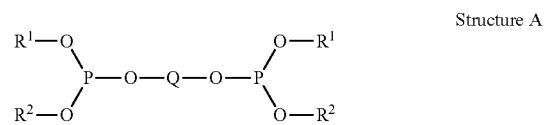

Structure A

The phosphite with bridging phenol ligand (CLS) as described above has the chemical structure shown below as Structure B, C, or D.

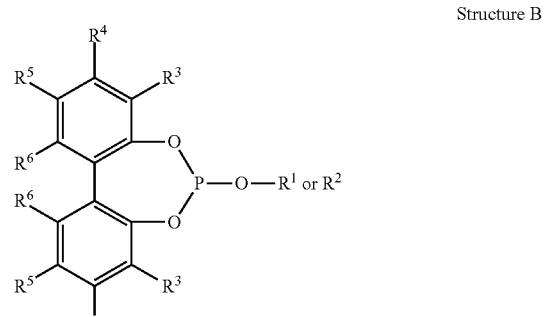

Structure B

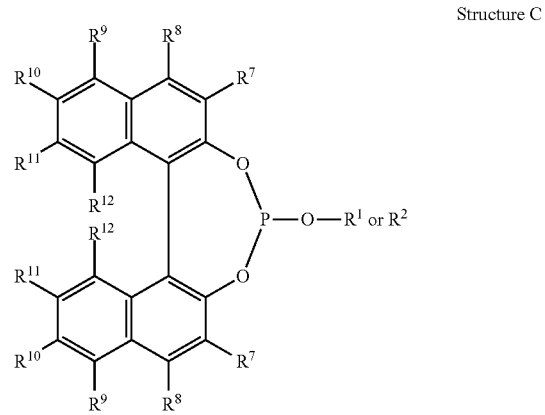

Structure C

-continued

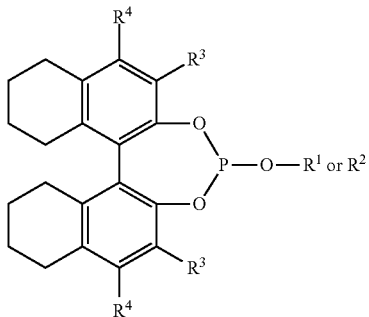

Structure D

The triaryl phosphite ligand structure (TLS) as described above has the chemical structure shown below as Structure E.

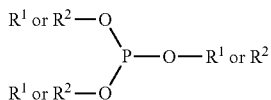

Structure E

As used herein a boiling point (BP) of a compound refers to the temperature at which a pure form of the compound boils at atmospheric pressure. A listed boiling point is the temperature of a boiling point for a compound listed in at least one reliable source from the chemical literature.

As used herein, the terms "distillation apparatus" and "distillation column" are used interchangeably, and both of these terms generally refer to equipment for performing distillation steps. For the purposes of this disclosure, a flasher is considered to be a distillation column.

The singular forms "a," "an" and "the" can include plural referents unless the context clearly dictates otherwise.

The term "about" can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "organic group" as used herein refers to but is not limited to any carbon-containing functional group. For example, an oxygen-containing group such as alkoxy groups, aryloxy groups, aralkyloxy groups, oxo(carbonyl) groups, carboxyl groups including carboxylic acids, carboxylates, and carboxylate esters; a sulfur-containing group such as alkyl and aryl sulfide groups; and other heteroatom-containing groups. Non-limiting examples of organic groups include OR', OC(O)N(R')$_2$, CN, CF$_3$, OCF$_3$, R', C(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen (in examples that include other carbon atoms) or a carbon-based moiety, and wherein the carbon-based moiety can itself be further substituted; for example, wherein R' can be hydrogen (in examples that include other carbon atoms), alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl, or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J. Examples of organic groups include linear and/or branched groups such as alkyl groups, fully or partially halogen-substituted haloalkyl groups, alkenyl groups, alkynyl groups, aromatic groups, acrylate functional groups, and methacrylate functional groups; and other organic functional groups such as ether groups, cyanate ester groups, ester groups, carboxylate salt groups, and masked isocyano groups. Examples of organic groups include, but are not limited to, alkyl groups such as methyl, ethyl, propyl, isopropyl, n-butyl, s-butyl, and t-butyl groups, acrylate functional groups such as acryloyloxypropyl groups and methacryloyloxypropyl groups; alkenyl groups such as vinyl, allyl, and butenyl groups; alkynyl groups such as ethynyl and propynyl groups; aromatic groups such as phenyl, tolyl, and xylyl groups; cyanoalkyl groups such as cyanoethyl and cyanopropyl groups; halogenated hydrocarbon groups such as 3,3,3-trifluoropropyl, 3-chloropropyl, dichlorophenyl, and 6,6,6,5,5,4,4,3,3-nonafluorohexyl groups; alkenyloxypoly(oxyalkyene) groups such as allyloxy(polyoxyethylene), allyloxypoly(oxypropylene), and allyloxy-poly(oxypropylene)-co-poly(oxyethylene) groups; alkyloxypoly(oxyalkyene) groups such as propyloxy (polyoxyethylene), propyloxypoly(oxypropylene), and propyloxy-poly(oxypropylene)-co-poly(oxyethylene) groups; halogen substituted alkyloxypoly(oxyalkyene) groups such as perfluoropropyloxy(polyoxyethylene), perfluoropropyloxypoly(oxypropylene), and perfluoropropyloxy-poly(oxypropylene)-co-poly(oxyethylene) groups; alkoxy groups such as methoxy, ethoxy, n-propoxy, isopropoxy, n-butoxy, and ethylhexyloxy groups; aminoalkyl groups such as 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole groups; epoxyalkyl groups such as 3-glycidoxypropyl, 2-(3,4-epoxycyclohexyl)ethyl, and 5,6-epoxyhexyl groups; ester functional groups such as actetoxyethyl and benzoyloxypropyl groups; hydroxy functional groups such as 2-hydroxyethyl groups; masked isocyanate functional groups such as propyl-t-butylcarbamate, and propylethylcarbamate groups; aldehyde functional groups such as undecanal and butyraldehyde groups; anhydride functional groups such as 3-propyl succinic anhydride and 3-propyl maleic anhydride groups; and metal salts of carboxylic acids such as the zinc, sodium, or potassium salts of 3-carboxypropyl and 2-carboxyethyl.

The term "substituted" as used herein refers to an organic group as defined herein or molecule in which one or more bonds to a hydrogen atom contained therein are replaced by one or more bonds to a non-hydrogen atom. The term "functional group" or "substituent" as used herein refers to a group that can be or is substituted onto a molecule, or onto an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups.

Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

The term "alkyl" as used herein refers to straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —CH≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R—NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $—NH_2$, $—NHR$, $—NR_2$, $—NR_3^+$, wherein each R is independently selected, and protonated forms of each, except for $—NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

The terms "halo" or "halogen" or "halide", as used herein, by themselves or as part of another substituent mean, unless otherwise stated, a fluorine, chlorine, bromine, or iodine atom, preferably, fluorine, chlorine, or bromine.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "monovalent" as used herein refers to a substituent connecting via a single bond to a substituted molecule. When a substituent is monovalent, such as, for example, F or Cl, it is bonded to the atom it is substituting by a single bond.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "solvent" as used herein refers to a liquid that can dissolve a solid, liquid, or gas. Nonlimiting examples of solvents are organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "ligand" as used herein refers to an ion or molecule that can bind to a central metal atom (e.g., Ni) to form a coordination complex.

In some examples, 3PN can be purchased commercially, or can be manufactured by reacting 1,3-butadiene (BD) and hydrogen cyanide (HC≡N) in a reaction zone under sufficient reaction conditions to produce a reaction product including 3-pentenenitrile (3PN) and 2-methyl-3-butenenitrile (2M3BN). The 2M3BN can be isomerized in a second reaction zone in the presence of a second catalyst under sufficient isomerization conditions to produce a reaction product including 3PN. The 3PN can be recovered from the effluents of both the first reaction zone and the second reaction zone.

GENERAL

Various embodiments relate to a process for making nitriles, including for example ADN and MGN, are described herein. In one embodiment, 3PN is a feedstock. Complexes of nickel and certain bidentate phosphite ligands, in the presence of a Lewis acid promoter, can catalyze the reaction of 3PN with HCN to make ADN. In order to most efficiently use a catalyst in the hydrocyanation of 3-pentenenitrile, recycle of the catalyst is desirable. Recycling the catalyst, however, can cause a loss in catalytic activity. At the same time, the catalyst can form degradation products. These degradation byproducts along with reaction byproducts can accumulate in the catalyst recycle loops along with catalyst. This decreases the overall catalytic activity of the circulating catalyst, both by reducing the amount of the desired nickel-ligand complex, and increasing the amount of degradation products that can be inert or actively deleterious to the efficiency of the hydrocyanation reaction. Accordingly, there is a need to limit the degradation of the nickel-ligand catalyst complex, especially for example in continuous operation.

The disclosed process can include continuously feeding 3-pentenenitrile and HCN to a hydrocyanation reaction zone that includes a Lewis acid promoter, nickel, and a phosphorus-containing ligand. In various embodiments, the process can also include controlling a water concentration within the hydrocyanation reaction zone sufficient to maintain a high activity of the ligand or catalyst through successive recycle cycles. In various embodiments, the process also can include controlling a water concentration within the hydrocyanation reaction zone to between about 0.5 ppm up to the saturation limit of the reaction mixture, for example 0.5 ppm to about and about 2000 ppm, or about 1 ppm and 1000 ppm, or from about 5 ppm to about 500 ppm, or from about 10 ppm to about 350 ppm, or from about 20 ppm to about 300 ppm, or at about 240 ppm, can help to suppress the degradation of catalytic activity of the recycled catalyst or of the catalyst derived from the recycled ligand. Preferably, the process controls the water concentration within the hydrocyanation reaction zone to about 100 ppm to about 300 ppm. In some embodiments, adding water to provide reactor concentrations of more than 2000 ppm water can trigger ligand degradation. Thus, in some embodiments, water concentrations near this range can benefit from careful attention and close process control. Water concentrations in the process can be determined using measures known to those skilled in the art. For example, water concentration can be determined by Karl Fischer Titration for water with introduction of the sample via azeotropic distillation.

Charging water to a hydrocyanation reaction zone is counterintuitive, because it is generally taught that water hydrolyzes phosphorus-containing ligands or otherwise causes or participates in the formation of undesirable byproducts. The mechanism of the degradation of the catalyst is not fully understood, nor is the role of water in inhibiting this degradation.

Phosphorus-Containing Ligand

The catalysts used in the disclosed process and/or products include nickel and at least one phosphorus-containing (P-containing) ligand, such as a phosphite, a phosphonite, a phosphinite, a phosphine, and a mixed P-containing ligand. In some embodiments, a catalyst can include one type of phosphorus-containing ligand. In other embodiments, the catalyst can include multiple types of phosphorus-containing ligands.

The P-containing ligands chemically bond to nickel to form a ligand-nickel catalyst complex. The P-containing ligands can be monodentate or multidentate, for example, bidentate or tridentate. The term "bidentate" is well known in the art and means both phosphorus atoms of the ligand can be bonded to a single metal atom. The term "tridentate" means the three phosphorus atoms on the ligand can be bonded to a single metal atom. The terms "bidentate" and "tridentate" are also known in the art to designate chelate ligands.

As used herein, the term "mixed P-containing ligand" means a P-containing ligand including at least one combination selected from the group consisting of a phosphite-phosphonite, a phosphite-phosphinite, a phosphite-phosphine, a phosphonite-phosphinite, a phosphonite-phosphine, and a phosphinite-phosphine.

In some embodiments, suitable phosphorus containing ligands include compounds having Formula (II). Formula (II) has the chemical structure

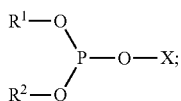

Formula (II)

wherein in Formula (II), $R^1$ and $R^2$ are the same or different, substituted or unsubstituted, monovalent aryl groups; $R^1$ and $R^2$ are bridged to one another or unbridged to one another; X is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, phosphitylbisaryl, phosphitylbisheteroaryl, hydroxybisaryl, hydroxybisheteroaryl, oxazole, amine, amide, nitrile, mercaptyl, and halogen groups.

In embodiments where X=phosphitylbisaryl, in some examples X can have a chemical structure selected from one of the following structures:

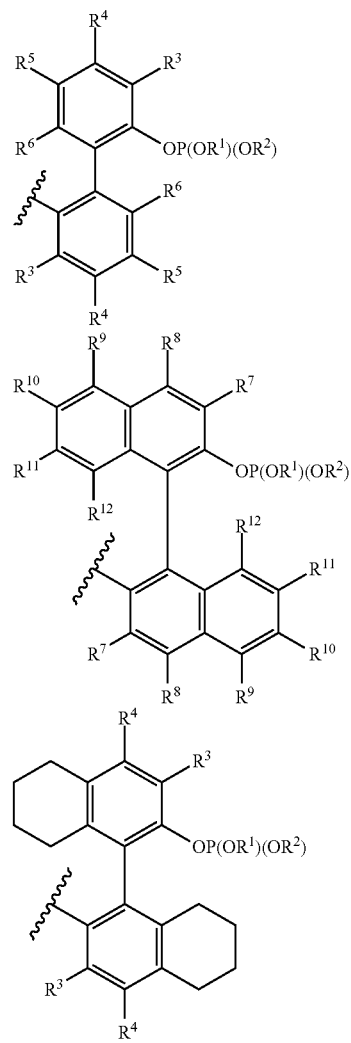

$R^1$ and $R^2$ are the same or different, substituted or unsubstituted, monovalent aryl groups; $R^1$ and $R^2$ are bridged to one another or unbridged to one another; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups.

In some embodiments, suitable phosphorus-containing ligands for the catalyst can be selected from the group consisting of compounds of Formulas (III)-(XI), including combinations thereof. Formula (III) has the structure:

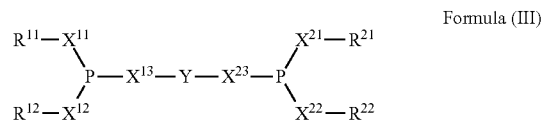

Formula (III)

wherein,
$X^{11}$, $X^{12}$, $X^{13}$, $X^{21}$, $X^{22}$ and $X^{23}$ independently represent oxygen or a single (direct) bond;
$R^{11}$ and $R^{12}$ independently represent identical or different, single or bridged organic radicals;

R21 and R22 independently represent identical or different, single or bridged organic radicals; and Y represents a bridging group.

In a particular embodiment, X11, X12, X13, X21, X22 and X23 can each be oxygen. In such a case, the bridging group Y is bonded to phosphite groups. In another embodiment, X11 and X12 can each be oxygen and X13 a single bond, or X11 and X13 each oxygen and X12 a single bond, so that the phosphorus atom surrounded by X11, X12 and X13 is the central atom of a phosphonite. In such a case, X21, X22 and X23 can each be oxygen, or X21 and X22 can each be oxygen and X23 a single bond, or X21 and X23 can each be oxygen and X22 a single bond, or X23 can be oxygen and X21 and X22 each a single bond, or X21 can be oxygen and X22 and X23 each a single bond, or X21, X22 and X23 can each be a single bond, so that the phosphorus atom surrounded by X21, X22 and X23 can be the central atom of a phosphite, phosphonite, phosphinite or phosphine, for example, a phosphonite. In another preferred embodiment, X13 can be oxygen and X11 and X12 each be a single bond, or X11 can be oxygen and X12 and X13 each a single bond, so that the phosphorus atom surrounded by X11, X12 and X13 is the central atom of a phosphinite. In such a case, X21, X22 and X23 can each be oxygen, or X23 can be oxygen and X21 and X22 each a single bond, or X21 can be oxygen and X22 and X23 each a single bond, or X21, X22 and X23 can each be a single bond, so that the phosphorus atom surrounded by X21, X22 and X23 can be the central atom of a phosphite, phosphinite or phosphine, for example a phosphinite. In another embodiment, X11, X12 and X13 can each be a single bond, so that the phosphorus atom surrounded by X11, X12 and X13 is the central atom of a phosphine. In such a case, X21, X22 and X23 can each be oxygen, or X21, X22 and X23 can each be a single bond, so that the phosphorus atom surrounded by X21, X22 and X23 can be the central atom of a phosphite or phosphine, for example a phosphine. The bridging group Y is particularly an arylene group which is substituted, for example by: $C_1$-$C_4$-alkyl; halogen, such as fluorine, chlorine, bromine; halogenated alkyl, such as trifluoromethyl; aryl, such as phenyl; or is unsubstituted, such as a group having from 6 to 20 carbon atoms in the aromatic system, in particular pyrocatechol, bis(phenol), bis(naphthol), or other bis-aryl systems. The $R^{11}$ and $R^{12}$ radicals can each independently be identical or different organic radicals. Advantageous $R^{11}$ and $R^{12}$ radicals can be aryl radicals, for example those having from 6 to 10 carbon atoms, which can be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{21}$ and $R^{22}$ radicals can each independently be identical or different organic radicals. Advantageous $R^{21}$ and $R^{22}$ radicals can be aryl radicals, particularly those having from 6 to 10 carbon atoms, which can be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{11}$ and $R^{12}$ radicals can each be separate or bridged. The $R^{21}$ and $R^{22}$ radicals can also each be separate or bridged. The $R^{11}$, $R^{12}$, $R^{21}$ and $R^{22}$ radicals can each be separate, two can be bridged and two separate, or all four can be bridged.

In some embodiments, Formula (III) can include a bidentate phosphorus-containing ligand, a diphosphite ligand structure (DLS), of Structure II,

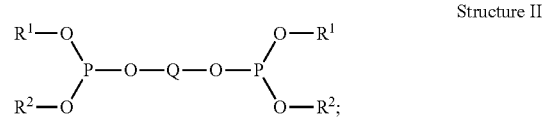

Structure II wherein in Structure II, O-Q-O is a divalent species of a bisaryl compound selected from the group consisting of Structure III, IV, or V,

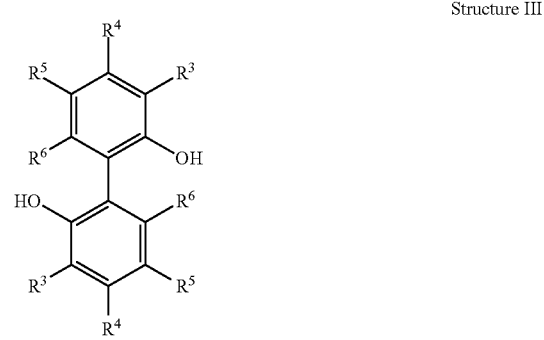

Structure III

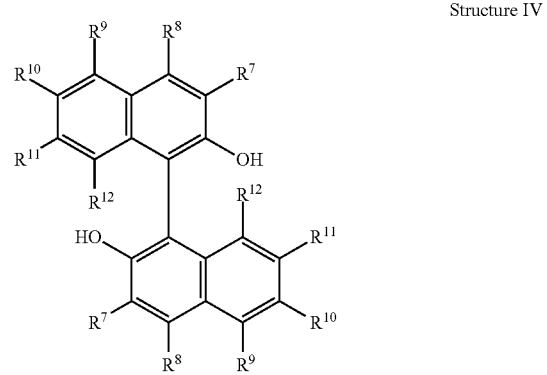

Structure IV

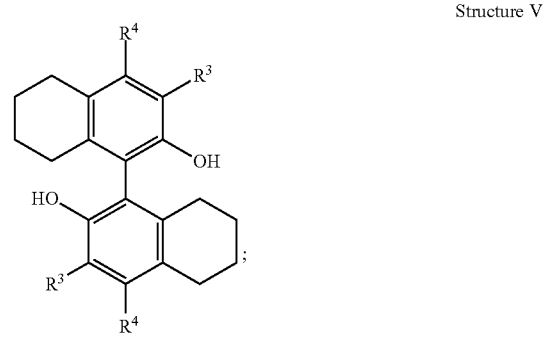

Structure V wherein in Structures II-V, $R^1$ and $R^2$ are the same or different, substituted or unsubstituted, monovalent aryl groups; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups.

Suitable ligands can also have the structure of Formula (IV),

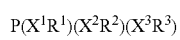

Formula (IV)

wherein,

X$^1$, X$^2$ and X$^3$ independently represent oxygen or a single direct bond; and R$^1$, R$^2$ and R$^3$ are each independently identical or different organic radicals.

In some examples, R$^1$, R$^2$ and R$^3$ are each independently alkyl radicals for example having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, for example having from 1 to 20 carbon atoms, such as 1,1'-biphenol, 1,1'-binaphthol. The R$^1$, R$^2$ and R$^3$ groups can be bonded together directly, e.g. not solely via the central phosphorus atom. In some examples, the R$^1$, R$^2$ and R$^3$ groups are not bonded together directly. In an embodiment, R$^1$, R$^2$ and R$^3$ groups are radicals selected from the group consisting of phenyl, o-tolyl, m-tolyl and p-tolyl. In a particular embodiment, a maximum of two of the R$^1$, R$^2$ and R$^3$ groups are phenyl groups. In another particular embodiment, a maximum of two of the R$^1$, R$^2$ and R$^3$ groups are o-tolyl groups.

In some examples, particular compounds which can be used are those of the formula (IVa) below:

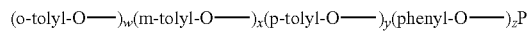

Formula (IVa)

where w, x, y, z are each a natural number and the following conditions apply: w+x+y+z=3 and z=less than or equal to 2.

Examples of such compounds (IVa) can include (o-tolyl-O—)$_3$P, (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P, or mixtures of such compounds.

An example of a bidentate phosphite ligand that can be useful in the present process is that having the Formula (V), shown below:

Formula (V)

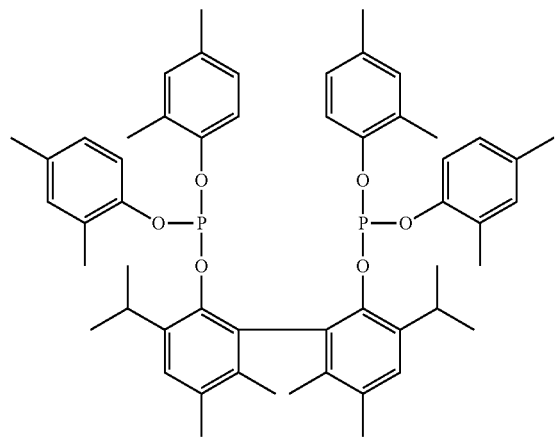

Further examples of bidentate phosphite ligands that are useful in the present process include those having the Formulae (VI) to (IX), shown below wherein for each formula, R$^{17}$ is selected from the group consisting of methyl, ethyl or iso-propyl, and R$^{18}$ and R$^{19}$ are independently selected from H or methyl:

Formula (VI)

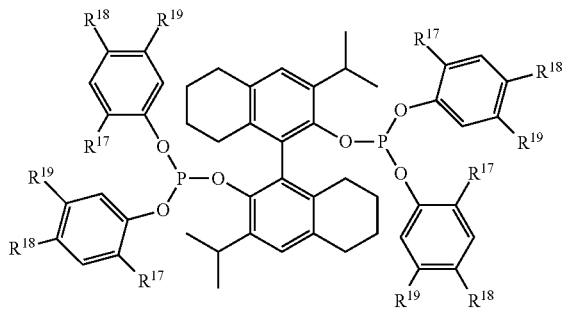

Formula (VII)

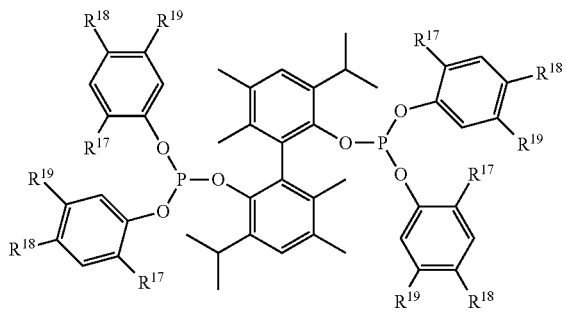

Formula (VIII)

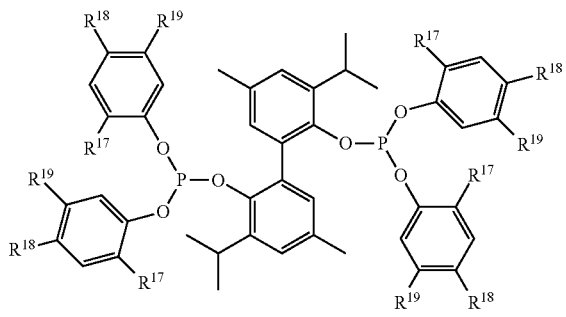

Formula (IX)

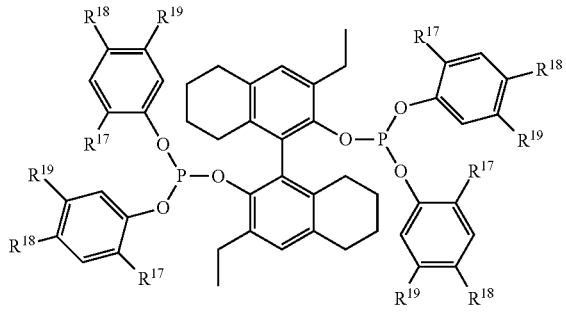

Additional examples of bidentate phosphite ligands that can be useful in the present process can include a ligand selected from a member of the group represented by Formulae (X) and (XI), in which all like reference characters have the same meaning, except as further explicitly limited:

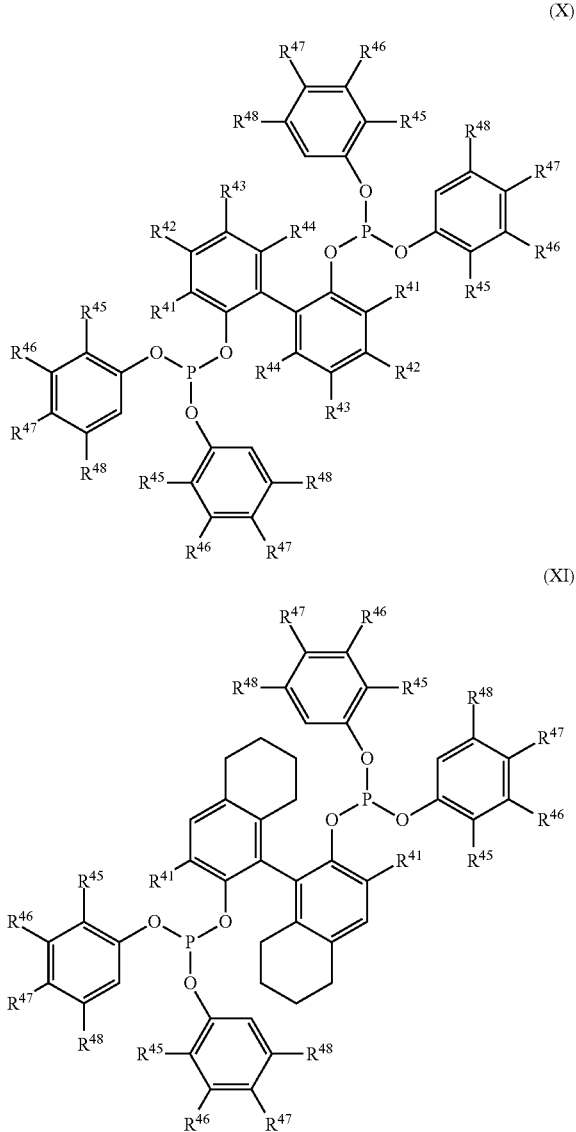

wherein, $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl. As used herein, "hydrocarbyl" particularly is alkyl or cycloalkyl.

In some examples, the bidentate phosphite ligand can be selected from a member of the group represented by Formula (X) and Formula (XI), wherein $R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$ and $R^{48}$ are independently selected from the group consisting of H and $C_1$ to $C_4$ hydrocarbyl.

As additional examples, the bidentate phosphite ligand can be selected from a member of the group represented by Formula (X), wherein $R^{41}$, $R^{44}$, and $R^{45}$ are methyl;
$R^{42}$, $R^{46}$, $R^{47}$ and $R^{48}$ are H; and
$R^{43}$ is a $C_1$ to $C_4$ hydrocarbyl;
or
$R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or t-butyl;
or the bidentate phosphite ligand can be selected from a member of the group represented by Formula XI, wherein
$R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand can be represented by Formula X, wherein $R^{41}$ is isopropyl; $R^{42}$, $R^{46}$, and $R^{48}$ are H; and $R^{43}$, $R^{44}$, $R^{45}$, and $R^{47}$ are methyl.

It will be recognized that the chemical structures given herein are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulae (V) to (XI), respectively, can bring the two phosphorus atoms of each Formula in closer proximity to one another and can allow the phosphite ligand to bind to nickel in a bidentate fashion. In addition, use of an optically active moiety such as for example sec-butyl for $R^{41}$ can result in optically active catalysts. In some examples, the use of asymmetric or optically active catalysts can result in stereospecific catalyst activity.

Lewis Acid Promoter

In various embodiments, the process of hydrocyanating 3-pentenenitrile to produce adiponitrile, can take place for example in the presence of a promoter for promoting the reaction, for example to allow the reaction to proceed or to increase the reaction rate of the reaction. The promoter can be a Lewis acid, such as an inorganic compound, an organometallic compound, or combinations thereof, in which a cation of the Lewis acid is selected from the group consisting of scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin. For example, the Lewis acid promoter can be zinc chloride or triphenylboron.

Preparation of the Nickel Catalyst Complex

The reaction of nickel metal with at least one free phosphorus-containing ligand is taught in, for example, U.S. Pat. Nos. 3,903,120, 4,385,007, 4,416,825; U.S. Patent Application Publication No. 20040176622, and PCT Patent Application Publication No. 1995011077, incorporated herein by reference.

Catalyst compositions including at least one phosphorus-containing ligand can be substantially free and maintained separate from at least one of, for example, carbon monoxide, oxygen, and water. These catalyst compositions can be preformed or prepared in situ according to techniques well-known in the art. For example, the catalyst composition can be formed by contacting a monodentate or bidentate phosphite ligand with a nickel compound having ligands easily displaced or replaced by organophosphite ligands, such as $Ni(COD)_2$, $Ni[P(O-o-C_6H_4CH_3)_3]_3$, and $Ni[P(O-o-$ C$_6$H$_4$CH$_3$)$_3$]$_2$(C$_2$H$_4$), all of which are well known in the art, wherein 1,5-cyclooctadiene (COD), tris(ortho-tolyl)phosphite [P(O-o-C$_6$H$_4$CH$_3$)$_3$], and ethylene (C$_2$H$_4$) can be examples of easily displaced ligands, where the lower case "o" represents ortho. Elemental nickel, for example nickel powder, when combined with a halogenated catalyst, for example as described in U.S. Pat. No. 3,903,120, can also be a suitable source of nickel.

In some examples, divalent nickel compounds can be combined with a reducing agent to serve as a source of nickel in the reaction. In some examples, the divalent nickel compounds can be combined with a reducing agent in the presence of a monodentate or bidentate phosphite ligand to form the nickel, which can then form a nickel-ligand complex. Examples of suitable divalent nickel compounds can include compounds of the formula NiZ$_2$ where Z is halide, carboxylate, or acetylacetonate. Examples of suitable reducing agents can include metal borohydrides, metal aluminum hydrides, metal alkyls, Li, Na, K, Zn, Fe or H$_2$ and electro-chemical means known from the art. See, for example, U.S. Pat. No. 6,893,996, which is incorporated herein by reference. In some examples, in a catalyst composition, the bidentate phosphite ligand can be present in excess of what can theoretically be coordinated to the nickel present in the mixture at a given time.

Some examples of suitable methods for preparing catalysts are described in WO2011/075494, WO2011/075496 and WO2012/033556.

In some examples, the catalyst composition can be dissolved in a solvent non-reactive toward, and miscible with, the hydrocyanation reaction mixture. Examples of suitable solvents can include, for example, aliphatic and aromatic hydrocarbons with 1 to 10 carbon atoms, and nitrile solvents such as acetonitrile. In some examples, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, can be used to dissolve the catalyst composition.

A more detailed description of a representative process for the manufacture of adiponitrile is made with reference to FIG. 1, which provides a simplified schematic representation of such a process. FIG. 1 shows a first reaction zone (Z1), where a mixture comprising 1,3-butadiene and hydrogen cyanide is contacted in the presence of a first catalyst, for example, comprising Ni and a first phosphorus-containing ligand, collectively a first catalyst system, to produce a reaction product substantially comprising 3-pentenenitrile (3PN) and 2-methyl-3-butenenitrile (2M3BN).

Figure 4:
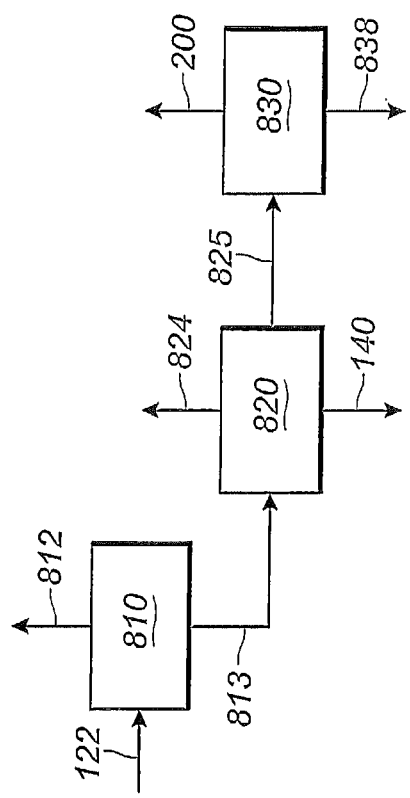
FIG. 4 is a representation of an example of separation section 125 shown in FIG. 1.

As shown in FIG. 1, 1,3-butadiene reactant is fed into the first reaction zone (Z1) through line 100, hydrogen cyanide reactant is fed into the first reaction zone (Z1) through line 120, and catalyst is fed into the first reaction zone (Z1) through line 140. A reaction product stream is taken from the first reaction zone (Z1) through line 122. The reaction product stream in line 122 comprises products, byproducts, unreacted reactants and catalyst, which flows through the first reaction zone (Z1). The reaction product stream 122 is introduced into a separation section 125, to obtain, inter alia, a concentrated catalyst stream 140 and product stream 200 comprising 2-methyl-3-butenenitrile (2M3BN). The separation section 125 may comprise one or more distillation columns. An example of separation section 125 is shown in FIG. 4. Unreacted hydrogen cyanide and 1,3-butadiene may also be separated from reaction products and catalyst in separation section 125. Unreacted 1,3-butadiene may be recycled to the first reaction zone (Z1) through lines not shown in FIG. 1. A stream comprising 3-pentenenitrile (3PN) may also be withdrawn from separation section 125 through a line not shown in FIG. 1. At least a portion of the catalyst separated from reaction products in separation section 125 may be recycled to the first reaction zone (Z1) through line 140.

Subsequent to the reaction in the first reaction zone (Z1), the substantial isomerization of 2M3BN in a second reaction zone (Z2) is conducted in the presence of an isomerization catalyst to produce a reaction product comprising substantially 3PN. The isomerization catalyst is also referred to herein as the second catalyst. The isomerization catalyst may be the same as the catalyst introduced into the first reaction zone (Z1). Optionally, the isomerization catalyst may be different from the catalyst introduced into the first reaction zone (Z1).

Figure 5:
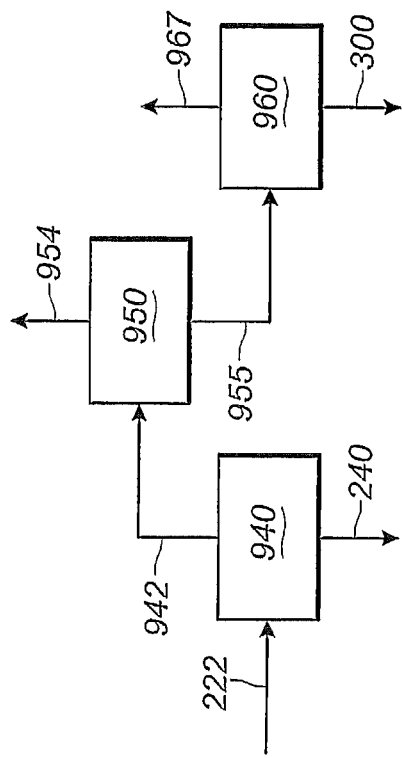
FIG. 5 is a representation of an example of separation section 225 shown in FIG. 1.

As shown in FIG. 1, a feed comprising 2M3BN is introduced into the second reaction zone (Z2) through line 200. Catalyst is introduced into the second reaction zone (Z2) through line 240. The effluent stream 222 from the second reaction zone (Z2) comprises catalyst and 3PN product. This effluent stream 222 passes into separation section 225 to obtain, inter alia, a 3PN product stream 300 and a concentrated catalyst stream 240. Separation section 225 may comprise one or more distillation apparatus. FIG. 5 shows an example of such a separation section 225.

Catalyst recycle systems are shown in FIG. 1 for supplying catalyst to the first reaction zone (Z1) and the second reaction zone (Z2). These catalyst recycle systems comprise further systems for purifying at least a portion of the catalyst prior to recycle.

In the catalyst recycle system for supplying catalyst to the first reaction zone (Z1), a portion of the concentrated catalyst stream in line 140 is diverted into catalyst purge stream 126.

Catalyst in purge stream 126 is in the form of a solution including impurities, such as reaction byproducts and catalyst degradation byproducts. Catalyst in purge stream 126 is fed to liquid/liquid extraction zone 150 to at least partially purify or regenerate the catalyst. The catalyst is purified or regenerated in that at least some byproducts are removed from the catalyst solution.

A non-polar solvent, such as an alkane, is fed into the liquid/liquid extraction zone 150 through line 130. A polar solvent, which is immiscible with the non-polar solvent, is also fed into the liquid/liquid extraction zone 150 through line 500.

In one embodiment, catalyst purge stream 126 and the polar solvent in line 500 are mixed prior to charging the combined stream to extraction zone 150. Although FIG. 1 schematically shows purge stream 126 and recycle stream 500 separately added to extraction zone 150, it is to be understood that catalyst purge stream 126 and the polar solvent in line 500 are preferably mixed before charging a combined stream to extraction zone 150.

In extraction zone 150, there is formed a non-polar phase comprising non-polar solvent and catalyst and a polar phase (e.g., a raffinate) comprising polar solvent and, for example, reaction byproducts and catalyst degradation products. The non-polar phase is taken from extraction zone 150 via line 134 to distillation apparatus 155. The polar phase is taken from extraction zone 150 via line 510 to separation section 1000.

Figure 2:
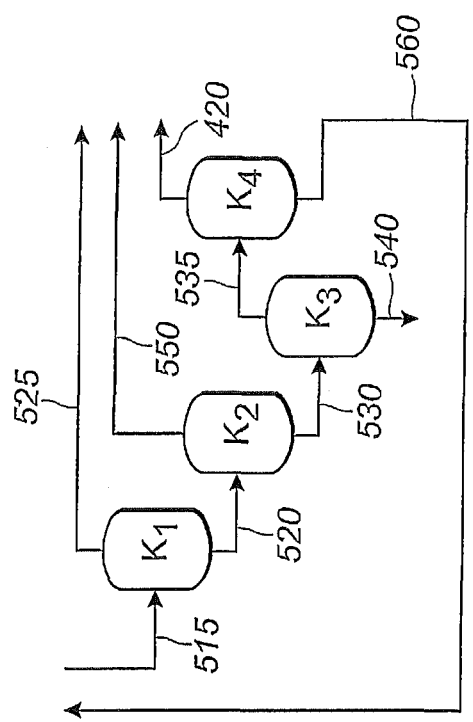
FIG. 2 is a representation of an example of separation section 1000 or separation section 2000 shown in FIG. 1.

An example of separation section 1000 is described in greater detail in FIG. 2. Separation section 1000 may include, collectively, a series of columns (K1, K2, K3 and K4) which provide for the removal of certain reaction byproducts and certain catalyst degradation products from the polar solvent.

The column bottom of K4 provides polar solvent, which is returned to extraction zone 150, via line 500.

Non-polar solvent is distillatively recovered in distillation apparatus 155 and returned to extraction zone 150, via line 130. Extraction zone 150, line 134, distillation apparatus 155 and line 130, collectively, form a recovery loop for recycling non-polar solvent into extraction zone 150. Extraction zone 150, line 510, separation section 1000 and line 500, collectively, form a recovery loop for recycling polar solvent into extraction zone 150. Additional non-polar solvent and polar solvent may be introduced into extraction zone 150 by lines not shown in FIG. 1. This additional solvent may be added for start up and for make-up of solvent lost during the course of the liquid/liquid extraction step.

Column bottoms from distillation column 155 include partially purified catalyst. This catalyst is partially purified or regenerated in the sense that at least some of the catalyst degradation products and/or reaction byproducts have been separated from the solution containing the catalyst. This partially purified catalyst may be taken from distillation column 155 through line 156 and introduced at any point for recycle into the first reaction zone (Z1). In FIG. 1, partially purified catalyst may be taken from distillation column 155 through line 156 and transferred into line 146 for introduction into catalyst recycle line 140 for recycle into the first reaction zone (Z1). FIG. 1 shows the introduction of stream 146 downstream of the take-off stream 126, but this stream may, optionally, be introduced upstream of the take-off stream 126. Stream 146 may also, optionally, be added to any catalyst-containing stream associated with the first reaction zone (Z1). Optionally, at least a portion of the partially purified catalyst stream in line 156 may be recycled into the second reaction zone (Z2). In FIG. 1, partially purified catalyst stream in line 156 may be transferred into line 246 for introduction into catalyst recycle line 240 for recycle into the second reaction zone (Z2). However, it will be understood that other routes, not shown in FIG. 1, may be used for routing partially purified first catalyst into the second reaction zone (Z2).

The partially purified stream of first catalyst, which is subsequently returned to the first reaction zone (Z1) or, optionally, to the second reaction zone (Z2), may be provided with additional Ni and/or additional phosphorus-containing ligand. In FIG. 1, additional Ni and/or additional phosphorus-containing ligand may be provided via line 145. Also as shown in FIG. 1, partially purified stream of first catalyst, which is subsequently fed to the second reaction zone (Z2), may be provided with additional Ni and/or phosphorus-containing ligand via line 245. However, it will be understood, that make-up catalyst may be added via different routes, not shown in FIG. 1. For example, make-up catalyst stream 145 may be charged to other sections of the first reaction zone catalyst loop or, for example, directly to the first reaction zone (Z1).

In a particular embodiment shown in FIG. 1, the second reaction zone (Z2) is provided with a second catalyst recovery system for supplying catalyst to the second reaction zone (Z2). In this second catalyst recycle system, a portion of the concentrated catalyst stream in line 240 is diverted into catalyst purge stream 226. This catalyst purge stream 226 is fed into liquid/liquid extraction zone 250. A non-polar solvent, such as an alkane, is fed into the liquid/liquid extraction zone 250 through line 230. A polar solvent, which is immiscible with the non-polar solvent, is also fed into the liquid/liquid extraction zone 250 through line 700. Dinitriles from sources not shown in FIG. 1 may be added to extraction zone 250, as needed to accomplish desired phase separation and extraction.

In one embodiment, catalyst purge stream 226 and the polar solvent in line 700 are mixed prior to charging the combined stream to extraction zone 250. Although FIG. 1 schematically shows purge stream 226 and recycle stream 700 separately added to extraction zone 250, it is to be understood that catalyst purge stream 226 and the polar solvent in line 700 are preferably mixed before charging a combined stream to extraction zone 250.

In one embodiment, a portion of the refined dinitrile product stream from the third reaction zone (Z3) may be used as a feed to extraction zone 250. For example, a side stream (not shown) may be taken from line 500 and introduced into extraction zone 250. In extraction zone 250, there is formed a non-polar phase comprising non-polar solvent and catalyst and a polar phase (e.g., a raffinate) comprising, for example, polar solvent, reaction byproducts and certain catalyst degradation products. The non-polar phase is taken from extraction zone 250 via line 234 to distillation apparatus 255. The polar phase is taken from extraction zone 250 via line 710 to separation section 2000. Separation section 2000 is described in greater detail in FIG. 2.

Separation section 2000 includes, collectively, a series of columns (K1, K2, K3 and K4) which provide for the separation of certain reaction by-products and catalyst degradation products. The column bottom of K4 provides polar solvent, which is returned to extraction zone 250, via line 700. Additional polar solvent, in the form of adiponitrile, as need for phase separation, may be provided from adiponitrile produced in the third reaction zone (Z3) through lines not shown in FIG. 1.

Non-polar solvent is distillatively recovered in distillation apparatus 255 and returned to extraction zone 250, via line 230. Extraction zone 250, line 234, distillation column 255 and line 230, collectively, form a recovery loop for recycling non-polar solvent into extraction zone 250. Extraction zone 250, line 710, separation section 2000 and line 700, collectively, form a recovery loop for recycling polar solvent into extraction zone 250.

Column bottoms from distillation column 255 include partially purified catalyst. This catalyst is partially purified or regenerated in the sense that at least some of the catalyst degradation products and/or reaction byproducts have been separated from the solution containing the catalyst. This partially purified catalyst may be taken from distillation apparatus 255 through line 248 for introduction into catalyst recycle line 240 for recycle into the second reaction zone (Z2). Optionally, a side stream may be taken from line 248 into line 247, and this side stream may be used as a catalyst feed to the first reaction zone (Z1), for example, by introducing the side stream from line 247 into line 146 or line 140. Any partially purified stream of catalyst, which is subsequently fed to the second reaction zone (Z2), may be provided with additional Ni and/or phosphorus-containing ligand, for example, via line 245. Although not shown in FIG. 1, line 245 may optionally be fed directly into line 246 or line 248 instead of line 240. Other ways of introducing make-up catalyst are known in the art and may be used.

Although not shown in FIG. 1, it is possible that the first reaction zone (Z1) and the second reaction zone (Z2) share a single catalyst recovery system. A shared catalyst recovery system may be desirable when the first and second phosphorus-containing ligands are the same. In such a shared system, the following features may be eliminated or shut down: lines 226, 230, 234, 247, 248, 700, and 710; extraction zone 250; distillation apparatus 255; and separation section 2000. Instead of taking a purge stream via line 226, a purge stream may be taken via line 227 and introduced into line 126 or directly into extraction zone 150. In such a shared catalyst recovery system, any partially purified catalyst stream entering the second reaction zone (Z2) would pass through lines 246 and 240 according to the configuration shown in FIG. 1.

The 3PN product in line 300 is introduced into the third reaction zone (Z3), where 3PN is reacted with HCN. 3PN from separation section 125 may also be introduced into the third reaction zone (Z3) through a line or lines not shown in FIG. 1. The HCN reactant feed is introduced into the third reaction zone (Z3) through line 220.

Water can be fed to the third reaction zone (Z3) through any suitable inlet line (not shown) consistent with good engineering practice for thorough mixing, safe operation and good process control. Means for injecting water include metering pumps and control valves. Water may be suitably charged directly into the 3PN product in line 300 for introduction into the third reaction zone (Z3).

A third catalyst comprising, for example, Ni and a third phosphorus-containing ligand, collectively a third catalyst system, and a Lewis acid promoter is introduced into the third reaction zone (Z3) through line 340. The reaction of 3PN and HCN in the third reaction zone (Z3) produces a reaction product containing adiponitrile. A reaction product stream is taken from the third reaction zone (Z3) by line 400. The reaction product stream comprises, for example, adiponitrile, catalyst, promoter, and unreacted reactants. The reaction product stream may optionally be passed through a separation section (not shown in FIG. 1) to remove unreacted reactants, prior to separation of catalyst from adiponitrile product.

Catalyst and adiponitrile product from the product stream in line 400 are passed into liquid/liquid extraction zone 370. A non-polar solvent, such as an alkane, is fed into the liquid/liquid extraction zone 370 through line 330. The non-polar solvent introduced into the liquid/liquid extraction zone 370 may have the same or different composition as the non-polar solvent introduced into the liquid/liquid extraction zone 150. Together, non-polar solvent from line 330 and adiponitrile product from line 400 comprise an extractant system of immiscible components. In extraction zone 370, there is formed a non-polar phase comprising non-polar solvent and catalyst and a polar phase (e.g., a raffinate) comprising adiponitrile, promoter and catalyst degradation products.

The non-polar phase is taken from extraction zone 370 via line 334 to distillation apparatus 375. The polar phase comprising adiponitrile is taken from extraction zone 370 via line 600 to adiponitrile purification section 3000. Adiponitrile purification section 3000 is described in greater detail in FIG. 3.

Adiponitrile purification section 3000 may include, collectively, a series of columns (K'1, K'2, K'3 and K'4) which provide for the separation of impurities, such as reaction byproducts and catalyst degradation products. The column bottom of K'4 provides the purified adiponitrile product, which is recovered in line 660. A portion of the purified adiponitrile product may optionally be returned to extraction zone 150 or extraction zone 250 (by lines not shown in FIG. 1) to facilitate phase separation in these extraction zones.

Non-polar solvent is distillatively recovered in distillation apparatus 375 and returned to extraction zone 370, via line 330. Extraction zone 370, line 334, distillation apparatus 375 and line 330, collectively, form a recovery loop for recycling non-polar solvent into extraction zone 370. Column bottoms from distillation column 375 include partially purified catalyst. This partially purified catalyst may be taken from distillation column 375 through line 340 for recycle of catalyst into the third reaction zone (Z3). The partially purified stream of third catalyst in line 340, which is subsequently returned to the third reaction zone (Z3), may be provided with make-up quantities of additional Ni and/or third phosphorus-containing ligand along with promoter. In FIG. 1, make-up quantities of additional Ni and/or third phosphorus-containing ligand and/or promoter may be added via line 345. However, it will be appreciated that there are other ways of introducing make-up catalyst and promoter. For example, all or a portion of the recycled catalyst stream 340 may be charged to a catalyst reactor to increase its nickel content and the effluent from the catalyst reactor may introduced at a suitable point.

OVERVIEW OF FIG. 2

FIG. 2 shows a distillation train, which may be used as separation section 1000 or separation section 2000, shown in FIG. 1. In FIG. 2, line 515 represents either line 510 or line 710 of FIG. 1. Line 515 transports a raffinate stream from either extraction zone 150 or extraction zone 250 into separation section 1000 or separation section 2000, as shown in FIG. 1. The raffinate stream in line 515 is first passed into distillation column K1, where extraction solvent is separated from higher boiling components of the raffinate stream. In particular, extraction solvent, such as cyclohexane, is withdrawn from distillation column K1 through line 525, and higher boiling components of the raffinate stream are withdrawn from distillation column K1 through line 520.

The solvent-depleted stream in line 520 is then passed into distillation column K2, where pentenenitrile is separated from higher boiling components remaining in the raffinate stream. In particular, pentenenitrile, such as 3PN and any 2M3BN, present is withdrawn from distillation column K2 through line 550, and higher boiling components of the raffinate stream are withdrawn from distillation column K2 through line 530.

The pentenenitrile-depleted stream in line 530 is then passed into distillation column K3, where dinitriles are separated from higher boiling components remaining in the raffinate stream. In particular, dinitriles, such as ADN and MGN, are withdrawn from distillation column K3 through line 535, and higher boiling components of the raffinate stream are withdrawn from distillation column K3 through line 540. These higher boiling components in line 540 may comprise, for example, catalyst degradation products.

The dinitrile-enriched stream in line 535 is then passed into distillation column K4, where adiponitrile is separated from lower boiling dinitriles, such as MGN. In particular, MGN is withdrawn from distillation column K4 through line 420. The MGN-containing stream in line 420 may also include C8H13C≡N compounds and phenolic compounds. An adiponitrile-enriched stream is withdrawn from distillation column K4 through line 560. In FIG. 2, line 560 represents either line 500 or line 700 of FIG. 1. As shown in FIG. 1, the adiponitrile-enriched stream in line 500 is recycled to the liquid/liquid extraction zone 150, and the adiponitrile-enriched stream in line 700 is recycled to the liquid/liquid extraction zone 250.

OVERVIEW OF FIG. 3

Figure 3:
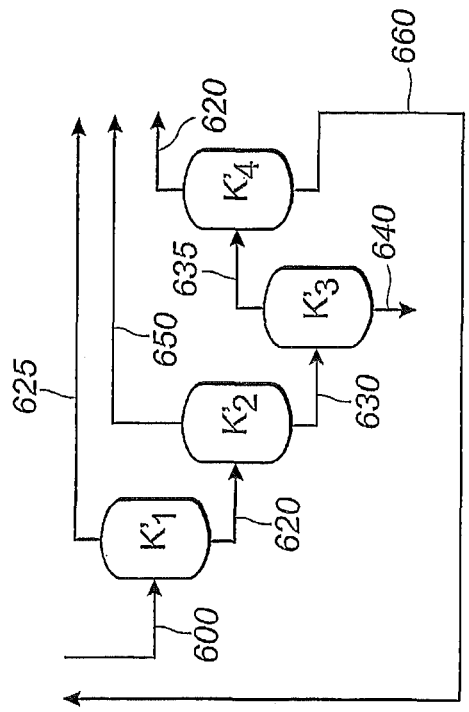
FIG. 3 is a representation of an example of adiponitrile purification section 3000 shown in FIG. 1.

FIG. 3 shows a distillation train, which may be used as adiponitrile purification section 3000, shown in FIG. 1. Line 600 transports a raffinate stream from extraction zone 370 into distillation column K'1, where extraction solvent is separated from higher boiling components of the raffinate stream. In particular, extraction solvent, such as cyclohexane, is withdrawn from distillation column K'1 through line 625, and higher boiling components of the raffinate stream are withdrawn from distillation column K'1 through line 620.

The solvent-depleted stream in line 620 is then passed into distillation column K'2, where pentenenitrile is separated from higher boiling components remaining in the raffinate stream. In particular, pentenenitrile, such as 3PN and any 2M3BN present, is withdrawn from distillation column K'2 through line 650, and higher boiling components of the raffinate stream are withdrawn from distillation column K'2 through line 630.

Stream 650 comprising 3PN, C2Pn, (E)2M2BN, (Z)2M2BN and VN is optionally fed to an additional separation system (not shown) prior to recycling recovered 3PN to reaction zone Z3 directly, or indirectly as a diluents in the product from the recovered catalyst stream from apparatus 375. A portion of the (E)2M2BN, (Z)$_2$M2BN, C2PN, and VN are removed to control their build-up. Unreacted water from reaction zone Z3 is contained in streams 625 and 650. Water removal from these streams can be included as part of this separation system.

The pentenenitrile-depleted stream in line 630 is then passed into distillation column K'3, where dinitriles are separated from higher boiling components remaining in the raffinate stream. In particular, dinitriles, such as ADN and MGN, are withdrawn from distillation column K'3 through line 635, and higher boiling components of the raffinate stream are withdrawn from distillation column K'3 through line 640. These higher boiling components in line 640 may comprise, for example, catalyst degradation products.

The dinitrile-enriched stream in line 635 is then passed into distillation column K'4, where adiponitrile is separated from lower boiling dinitriles, such as MGN. In particular, MGN is withdrawn from distillation column K'4 through line 650, and a purified adiponitrile stream is withdrawn from distillation column K'4 through line 660.

OVERVIEW OF FIG. 4

FIG. 4 is a schematic representation of an example of a distillation train, which may be used as separation section 125, shown in FIG. 1. Stream 122 comprising 3PN, 2M3BN, at least one catalyst, and BD is transferred into an apparatus 810 for distillation. In this apparatus, stream 122 is distilled to obtain a BD-enriched stream 812 and a BD-depleted stream 813 comprising 3PN, 2M3BN, and at least one catalyst. The BD-enriched stream 812 may be recycled to the first reaction zone (Z1).

The BD-depleted stream 813, which comprises 3PN, 2M3BN, and at least one catalyst is then transferred to another apparatus 820 for further distillation. In this apparatus, stream 813 is distilled to obtain a top product stream 824 enriched in BD, a stream 825, comprising 3PN and 2M3BN, and a bottom product stream 140 enriched in at least one catalyst. Stream 824 enriched in BD may also be recycled to the first reaction zone (Z1). If excess dinitriles are introduced into apparatus 820, the catalyst may thermally degrade, causing nickel and ligand to disassociate and resulting in plating out of nickel on high-temperature surfaces such as exchanger tubes and reboiler wall surfaces or, alternatively, trigger precipitation of nickel solids, for example, in the column bottoms.

Stream 825, comprising 3PN and 2M3BN, is transferred at least in part to another distillation apparatus 830. In this apparatus, the distillation of stream 825 is distilled to obtain 2M3BN-enriched stream 200 and 2M3BN-depleted stream 838 comprising 3PN. As described in the "Nylon Intermediates Refining" section of the PhD thesis dissertation by Decio Heringer Coutinho, University of Texas at Dallas, December 2001, stream 200 may be obtained at the top region of the distillation apparatus, while the stream 838 may be obtained at the bottom region of the distillation apparatus.

FIG. 4 illustrates one distillation system for distilling the effluent from the first reaction zone (Z1). However, it will be understood that it is within the skill in the art to design and operate other distillation systems to achieve the same or essentially the same results. For example, depending upon the thermal stability of catalyst, it may be possible to combine distillation apparatus 810 and distillation apparatus 820 into a single distillation apparatus, where a BN-enriched stream is withdraw as a top draw, a PN-enriched stream is withdrawn as a side draw, and a catalyst-enriched stream is withdrawn as a bottom draw.

OVERVIEW OF FIG. 5

FIG. 5 is a schematic representation of an example of a distillation train, which may be used as separation section 225, shown in FIG. 1. The isomerization reaction effluent in stream 222 obtained in the second reaction zone is distilled to recover catalyst and products. In a distillation step not shown in FIG. 5, light boilers may first be removed from stream 222. Low boilers are compounds which boil at temperatures less than pentenenitriles. Examples of light boilers include, butane, butadiene and cyclohexane. Compounds in stream 222, which boil at the same temperature or higher than pentenenitrile, are introduced into distillation apparatus 940. A pentenenitrile-enriched stream 942, comprising 3PN, 2M3BN, and (Z)-2M2BN, may be obtained from the distillation apparatus 940. Stream 942 may also comprise other pentenenitriles, selected from 4PN, (E)-2M2BN, or a combination thereof, and optionally dimerized BD compounds having the empirical formula C8H12, such as VCH and ethylidene cyclohexene isomers. A pentenenitrile-depleted stream 240, enriched in at least one catalyst, may be obtained as the bottom product.

U.S. Pat. No. 3,852,329 describes a process for "reduced loss to undesirable products such as 2-methyl-2-buteneni-trile." An objective of the distillation of stream 942 is to purge at least a portion of the lower-boiling (Z)-2M2BN isomer from the 3PN and 2M3BN reaction product mixture.

Stream 942, comprising 3PN, 2M3BN, and (Z)-2M2BN, is distilled in distillation apparatus 950. Stream 954 is obtained as an overhead product that is enriched in (Z)-2M2BN. Stream 955, comprising 3PN and 2M3BN, is obtained as a bottom product and is depleted in (Z)-2M2BN. "Enriched" and "depleted" in (Z)-2M2BN are relative to its concentration in stream 942.

Stream 954 may also comprise other pentenenitriles, selected from the group comprising 2M3BN, (E)-2M2BN, and optionally dimerized BD compounds having the empirical formula C8H12, such as VCH and ethylidene cyclohexene isomers. Stream 955 may also comprise other pentenenitriles, selected from the group comprising 4PN, 2PN, and (E)-2M2BN.

In one embodiment, the distillation is operated in such a manner to cause dimerized BD compounds to be enriched in stream 954 and depleted in stream 955, both relative to the concentration of dimerized BD compounds in stream 942. In another embodiment, dimerized BD compounds are enriched in stream 954 through an azeotrope of said compounds with 2M3BN. In another embodiment, stream 954 comprises greater than 1% by weight, for example greater than 5% by weight, for example greater than 10% by weight of 2M3BN, relative to the total mass of stream 954.

Stream 955, comprising 3PN and 2M3BN, may be transferred at least in part to distillation apparatus 960. In this apparatus, the distillation of stream 955 occurs to obtain 2M3BN-enriched stream 967 and a 2M3BN-depleted stream 300 comprising 3PN. As described in the "Nylon Intermediates Refining" section of the PhD thesis dissertation by Decio Heringer Coutinho, University of Texas at Dallas, December 2001, stream 967 may be obtained at the top region of the distillation apparatus, while the stream 300 may be obtained at the bottom region of the distillation apparatus.

FIG. 5 illustrates one distillation system for distilling the effluent from the second reaction zone (Z2). However, it will be understood that it is within the skill in the art to design and operate other distillation systems to achieve the same or essentially the same results. For example, a distillation step to remove low boilers may be inserted into the system, as described above. It is also possible to share equipment used for distilling the effluent from the first reaction zone. For example, a stream comprising 3PN and 2M3BN obtained by distilling the effluent from the second reaction zone (Z2) may be passed to a distillation apparatus, such as distillation apparatus 830, used in the distillation of the effluent form the from the first reaction zone (Z1), to obtain a 3PN-enriched stream and a 2M3BN-enriched stream.

Examples

Embodiments of the present invention are not limited by any theory of operation as given herein.

Fresh ligand was prepared according to the procedure published in WO2011/075494, WO2011/075496 and WO2012/033556. Fresh ligand solution was a mixture in cyclohexane with the major component (exclusive of solvent) being DLS, but also including TLS, CLS, and hydrolysis products of DLS, TLS, or CLS, and other products derived from DLS, TLS, CLS, or starting materials for DLS synthesis. An example composition of the fresh ligand solution is given in Table 1.

TABLE 1

Composition of the fresh ligand solution on a solvent free basis, wt %

| DLS | TLS | CLS | DLS – LHP |
|---|---|---|---|
| 80 | 15 | 2.7 | 2.3 |

Active Ni metal was prepared from basic nickel carbonates as described in WO2011/075494, WO2011/075496 and WO2012/033556.

An integrated experimental unit is used to study the stability of catalyst complex useful for hydrocyanation of pentenenitriles to adiponitrile. The unit includes several unit operations including a hydrocyanation reactor, a catalyst recovery system, and a catalyst preparation reaction and refining system. The unit is operated continuously for several weeks to understand the impact of time on stream (e.g., the impact of repeated recycle cycles) on the stability of the catalyst complex.

Hydrogen cyanide, catalyst complex solution, zinc chloride, water and pentenenitriles are fed to the hydrocyanation reactor where hydrocyanation of pentenenitriles to dinitriles takes place. The reaction is carried out at about 55° C. During hydrocyanation reaction a portion of the nickel is converted to nickel cyanide and degradation of the DLS takes place. The reactor effluent includes hydrocyanation reaction product adiponitrile, catalyst, ligand, unreacted pentenenitriles, ligand degradation products and nickel cyanide.

The catalyst and ligand are recovered from the reactor product in the catalyst recovery system. The catalyst recovery system includes three stages of mixers/settlers and cyclohexane to recover the catalyst and ligand from the reactor effluent. Also make-up fresh ligand is added to the mixer settlers. Fresh ligand as a solution in cyclohexane is added to the process at a rate equal to the consumption of DLS in the process. In addition to bidentate phosphite ligand, the fresh ligand solution includes ligand synthesis byproducts such as CLS and TLS and their degradation products, the composition of which is given in Table 1. Distribution co-efficients for these compounds are given in Table 2. Distribution co-efficients are defined as given below.

$$\text{Distribution co-efficient } (KLL) = \frac{\text{Wt \% of component in Extract phase}}{\text{Wt \% of component in raffinate phase}} \quad (5)$$

TABLE 2

| KLL at 65° C. | | | | |
|---|---|---|---|---|
| DLS | CLS | TLS | DLS – LHP | DLS – LHP |
| 100 | 20 | 8 | 25 | |

As shown in Table 2 some of these products have high extraction co-efficients; high extraction co-efficients can allow an increase in the extraction efficiency. Low extraction co-efficients can allow purging of unwanted reaction by-products from the recycle loop. As shown in Table 2 the ligand by-products CLS, TLS and DLS-LHP have relatively high extraction co-efficients and therefore are not effectively removed from the process and build-up in the recycle loop.

During hydrocyanation of pentenenitriles in the reactor degradation of ligand, DLS is observed. Examples of major pathways for DLS consumption are provided in Equations 6 and 7:

$$DLS \rightarrow CLS + TLS \quad (6)$$

$$DLS + H2O \rightarrow DLS-LHP + 2,4\text{-xylenol} \quad (7)$$

$$DLS + O_2 \rightarrow DLS \text{ oxide} \rightarrow DLS \text{ dioxide} \quad (8).$$

While not to limit the invention by a recitation of theory, Equation 8 is not believed to be a major pathway for DLS degradation as the hydrocyanation reaction is performed under air free conditions. Percent DLS disproportionation to CLS and TLS according to Equation 6 is estimated from a molar ratio of DLS/(DLS+TLS+CLS) as given is Equation 9.

$$\% \text{ change in } DLS = 100 * \frac{((DLS/(DLS + TLS + CLS))_{feed}) - ((DLS/(DLS + TLS + CLS))_{product})}{((DLS/(DLS + TLS + CLS))_{feed})} \quad (9)$$

Percent DLS hydrolysis to DLS-LHP according to equation 7 is estimated as given in Equation 10

$$\% \text{ change in } DLS = 100 * \frac{((DLS/(DLS + LHPD2))_{feed}) - ((DLS/(DLS + LHPD2))_{product})}{((DLS/(DLS + LHPD2))_{feed})}. \quad (10)$$

Overall change in DLS across the reactor is estimated from Equation 11

$$\% \text{ change in } D80 = \quad (11)$$
$$100 * \frac{((DLS/(DLS + TLS + CLS + LHPD2))_{feed}) - ((DLS/(DLS + TLS + CLS + LHPD2))_{product})}{((DLS/(DLS + TLS + CLS + LHPD2))_{feed})}.$$

Experiments are conducted at three different water concentrations and the results are provided in Table 3. As shown in the table, with very little water (about 20 ppm), the percent change in DLS due to disproportionation to CLS and TLS (Equation 6) is greater than the change in DLS observed due to hydrolysis (Equation 7). The amount of DLS change due to disproportionation to CLS and TLS is decreased by adding water to the reactor.

TABLE 3

Summary of DLS re-arrangement as a function of water under continuous operation with catalyst recovery and recycle.

| | % change in DLS | | |
|---|---|---|---|
| Water, ppm | DLS/ (DLS + TLS + CLS) | DLS/ (DLS + DLS − LHP) | DLS/(DLS + DLS − LHP + TLS + CLS) |
| 20 | 7.34 | 0.16 | 7.31 |
| 60 | 1.87 | 4.01 | 3.69 |
| 240 | 0.66 | 2.22 | 1.97 |

Concentration of CLS and TLS increases in the recycle loop as these compounds were also formed in the hydrocyanation reaction according to Equation 6. Under conditions where the bidentate phosphite degradation rate to CLS and TLS is high, the overall quality of ligand in recycle loop decreases (DLS/(DLS+CLS+TLS). The change in recycle ligand quality as a function of recycle catalyst turnovers when the DLS disproportionation rate to CLS and TLS is about 7.3 is given in Table 4. As shown in Table 4, the recycle ligand quality decreases with the number of recycle cycles (e.g., with time on stream). This can be due to the generation of TLS and CLS in the hydrocyanation reactor at a rate greater than they can be purged from the system through the extraction. The inert build-up in the recycle loop can have an effect on the process stability.

The effect of water on recycle ligand quality is also shown in Table 4. Recycle ligand quality is stabilized by causing the water concentration in the hydrocyanation reactor to be about 240 ppm. As shown in Table 3, the addition of water decreases the percent of DLS disproportionation to CLS and TLS. The overall consumption of DLS is improved in the presence of water. By increasing the water concentration to about 240 ppm, DLS degradation due to disproportionation to CLS and TLS decreases from about 7.3% to about 0.66%. Under the same conditions, DLS degradation due to hydrolysis increases from about 0.16% to about 2.2%. Overall change in DLS estimates according to Equation 6 is also provided in Table 3. Increasing the water concentration from about 20 ppm to about 240 ppm decreased the total percent change in DLS from about 7.3% to about 1.97%.

TABLE 4

Impact of water on the recycle ligand quality as a function of time on stream as estimated by DLS/(DLS + CLS + TLS)

| | Water concentration in the reaction zone, ppm | |
|---|---|---|
| Number of recycle cycles | 20 | 240 |
| 0 | 0.49 | 0.61 |
| 3 | 0.42 | 0.62 |

While the illustrative embodiments of the invention have been described with particularity, it will be understood that the invention is capable of other and different embodiments and that various other modifications will be apparent to and can be readily made by those skilled in the art without departing from the spirit and scope of the invention. Accordingly, it is not intended that the scope of the claims be limited to the examples and descriptions set forth herein but rather that the claims be construed as encompassing all the features of patentable novelty which reside in the present disclosure, including all features which would be treated as equivalents thereof by those skilled in the art to which the invention pertains.

Additional Embodiments

The present invention provides for the following exemplary embodiments, the numbering of which is not to be construed as designating levels of importance.

Embodiment 1 provides a process for hydrocyanating 3-pentenenitrile in a reaction zone in the presence of a catalyst complex comprising a phosphorus-containing ligand and nickel metal, said process comprising: flowing 3-pentenenitrile, Lewis acid, HCN and a controlled amount of water to the reaction zone; withdrawing reactor effluent comprising hydrocyanation product and catalyst complex from the reaction zone; contacting the reactor effluent with extraction solvent to recover catalyst complex and remove impurities from the catalyst complex; and recycling at least a portion of the recovered catalyst complex to the reaction zone.

Embodiment 2 provides the process of embodiment 1, wherein phosphorus-containing ligand has a chemical structure of Structure I,

Structure I wherein in Structure I, $R^1$ and $R^2$ are the same or different, substituted or unsubstituted, monovalent aryl groups; $R^1$ and $R^2$ are bridged to one another or unbridged to one another; X is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, phosphitylbisaryl, phosphitylbisheteroaryl, hydroxybisaryl, hydroxybisheteroaryl, oxazole, amine, amide, nitrile, mercaptyl, and halogen groups.

Embodiment 3 provides the process of any one of Embodiments 1-2, wherein the phosphorus-containing ligand is a bidentate phosphorus-containing ligand having aromatic termini that are connected through a phosphorus-containing backbone linkage.

Embodiment 4 provides the process of any one of Embodiments 1-3, wherein the phosphorus-containing ligand is a bidentate phosphorus-containing ligand of Structure II,

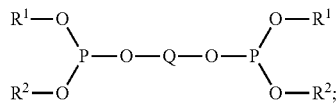

Structure II wherein in Structure II, O-Q-O is a divalent species of a bisaryl compound selected from the group consisting of Structure III, IV, or V,

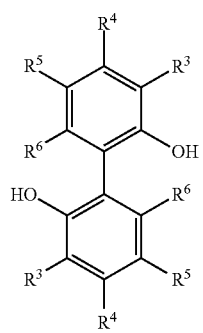

Structure III

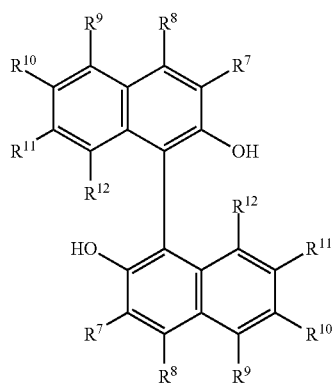

Structure IV

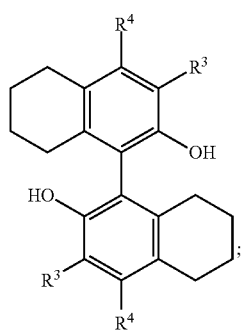

Structure V wherein in Structures II-V, $R^1$ and $R^2$ are the same or different, substituted or unsubstituted, monovalent aryl groups; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups.

Embodiment 5 provides the process of any one of Embodiments 1-4, wherein the phosphorus-containing ligand is a bidentate phosphorus-containing ligand of Structure VI,

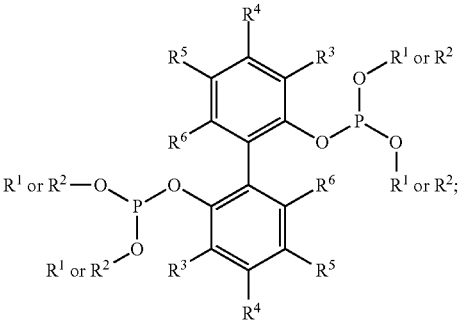

Structure VI wherein $R^1$ and $R^2$ are the same or different, substituted or unsubstituted, monovalent aryl groups; each of $R^3$, $R^4$, $R^5$, $R^6$ is independently selected from the group consisting of hydrogen and $C_{1-10}$ alkyl.

Embodiment 6 provides the process of any one of Embodiments 1-5, wherein the phosphorus-containing ligand is a bidentate phosphorus-containing ligand of Structure VII,

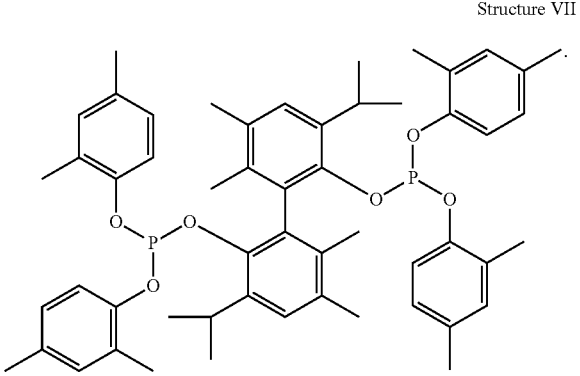

Structure VII

Embodiment 7 provides the process of any one of Embodiments 1-6, wherein the Lewis acid promoter includes triphenylboron or zinc chloride.

Embodiment 8 provides the process of any one of Embodiments 1-7 further including controlling the water concentration within the hydrocyanation reaction zone to be 0.5 ppm up to the saturation limit of the reaction mixture, for example 0.5 ppm to about and about 2000 ppm, or about 1 ppm and 1000 ppm, or from about 5 ppm to about 500 ppm, or from about 10 ppm to about 350 ppm, or from about 20 ppm to about 300 ppm, or at about 240 ppm.

Embodiment 9 provides the process of any one of Embodiments 1-8 further including controlling the water concentration within the hydrocyanation reaction zone to be between about 200 ppm and about 350 ppm.

Embodiment 10 provides the process of any one of Embodiments 1-9 further including removing water from a reaction zone effluent of the hydrocyanation reaction zone.

Embodiment 11 provides the process of Embodiment 10 wherein the step of removing water further includes removing water from the reaction zone effluent sufficiently to suppress hydrolysis of the phosphorus-containing ligand in processing downstream of the hydrocyanation reaction zone.

Embodiment 12 provides the process of Embodiment 11 wherein processing downstream of the hydrocyanation reaction zone includes a liquid-liquid extraction of the phosphorus-containing ligand from a dinitrile derived from the 3-pentenenitrile using a hydrocarbon extraction solvent.

Embodiment 13 provides the process of any one of Embodiments 1-12 wherein processing downstream of the hydrocyanation reaction zone includes distillation.

Embodiment 14 provides the process of any one of Embodiments 1-13, wherein controlling the water concentration includes adding water to the hydrocyanation reaction zone to maintain a water concentration within the reaction zone sufficient to suppress conversion of the phosphorus-containing ligand to a phosphorus-containing species that forms a ligand-metal complex less catalytically active with respect to pentenenitrile hydrocyanation than a catalyst formed from the phosphorus-containing ligand in the reactor feed.

Embodiment 15 provides the process of any one of Embodiments 1-14, wherein controlling the water concentration includes adding water to the hydrocyanation reaction zone to maintain a water concentration within the reaction zone sufficient to suppress formation of one or more products, derived from the phosphorus-containing ligand or derived from a catalyst formed from the ligand, that cause decreased catalytic activity of a catalyst mixture recycled from a reaction zone effluent of the hydrocyanation reaction zone or decreased catalytic activity of a catalyst mixture formed from a phosphorus-containing ligand mixture recycled from the reaction zone effluent of the hydrocyanation reaction zone with respect to pentenenitrile hydrocyanation as compared to a catalyst formed from the phosphorus-containing ligand.

Embodiment 16 provides a process for hydrocyanating 3-pentenenitrile including: feeding 3-pentenenitrile and HCN to a hydrocyanation reaction zone including a Lewis acid promoter, nickel and a bidentate phosphorus-containing ligand having Structure II,

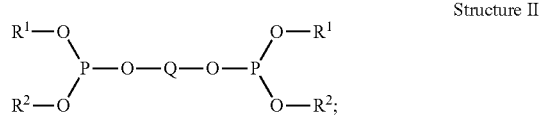

Structure II wherein in Structure II, O-Q-O is a divalent species of a bisaryl compound selected from the group consisting of Structure III, IV, or V,

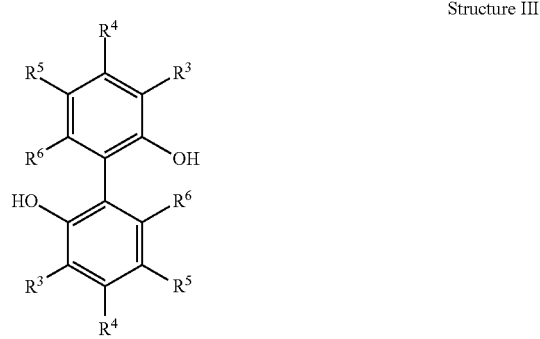

Structure III

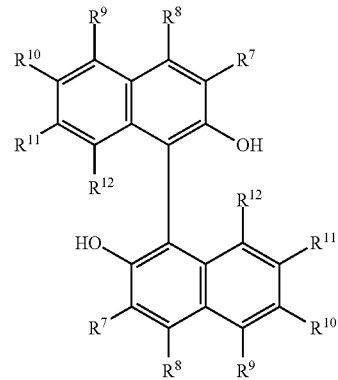

Structure IV

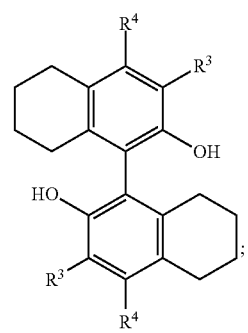

Structure V wherein in Structures II-V, $R^1$ and $R^2$ are the same or different, substituted or unsubstituted, monovalent aryl groups; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups; adding water to the hydrocyanation reaction zone to maintain a water concentration within the reaction zone sufficient to suppress conversion of the bidentate phosphorus-containing ligand to a phosphorus-containing species that forms a ligand-metal complex less catalytically active with respect to pentenenitrile hydrocyanation than a catalyst formed from the phosphorus-containing ligand; and removing sufficient water from a reaction zone effluent of the hydrocyanation reaction zone to suppress hydrolysis of the bidentate phosphorus-containing ligand in processing downstream of the hydrocyanation reaction zone.

Embodiment 17 provides the process of Embodiment 16 further including controlling the water concentration within the hydrocyanation reaction zone to be between about 100 ppm and about 400 ppm.

Embodiment 18 provides the process of any one of Embodiments 16-17 further including controlling the water concentration within the hydrocyanation reaction zone to be between about 200 ppm and about 350 ppm.

Embodiment 19 provides the process of any one of Embodiments 16-18 wherein the wherein processing downstream of the hydrocyanation reaction zone includes a liquid-liquid extraction of the bidentate phosphorus-containing ligand from a dinitrile derived from the 3-pentenenitrile using a hydrocarbon extraction solvent.

Embodiment 20 provides the process of any one of Embodiments 16-19 wherein processing downstream of the hydrocyanation reaction zone includes distillation.

Embodiment 21 provides a process for hydrocyanating 3-pentenenitrile including: feeding 3-pentenenitrile and HCN to a hydrocyanation reaction zone including a Lewis acid promoter, nickel and a bidentate phosphorus-containing ligand having Structure VII,

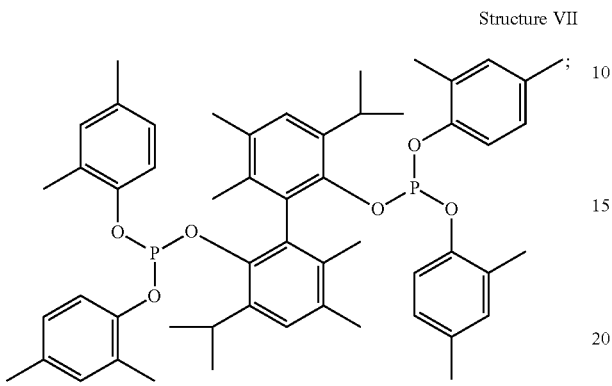

Structure VII adding water to the hydrocyanation reaction zone to maintain a water concentration within the reaction zone between about 100 ppm and about 400 ppm, sufficient to suppress conversion of the bidentate phosphorus-containing ligand to a phosphorus-containing species that forms a ligand-metal complex less catalytically active with respect to pentenenitrile hydrocyanation than a catalyst formed from the phosphorus-containing ligand; and removing sufficient water from a reaction zone effluent of the hydrocyanation reaction zone to suppress hydrolysis of the bidentate phosphorus-containing ligand in a processing downstream of the hydrocyanation reaction zone including liquid-liquid extraction of the phosphorus-containing ligand from a dinitrile derived from the 3-pentenenitrile using a hydrocarbon extraction solvent or in a processing downstream of the hydrocyanation reaction zone including distillation.

Embodiment 22 provides the apparatus or method of any one or any combination of Embodiments 1-21 optionally configured such that all elements or options recited are available to use or select from.

What is claimed is:

1. A process for hydrocyanating 3-pentenenitrile in a reaction zone in the presence of a catalyst complex comprising a phosphorus-containing ligand and nickel metal, said process comprising:
    a. charging the catalyst complex, 3-pentenenitrile, a Lewis acid and HCN to the reaction zone;
    b. withdrawing reactor effluent comprising hydrocyanation product and catalyst complex from the reaction zone;
    c. contacting the reactor effluent with an extraction solvent to recover catalyst complex and remove impurities from the catalyst complex; and
    d. recharging at least a portion of the recovered catalyst complex to the reaction zone,
    e. establishing disproportionation and hydrolysis deactivation percentages of the catalyst complex for the particular process, and
    f. controlling the amount of water in the catalyst complex recharged to the reaction zone in step d. to decrease the total percentage deactivation percentages established in step e.

2. The process of claim 1, wherein the controlling of the amount of water in step f. is by adding water.

3. The process of claim 1, wherein the controlling of the amount of water in step f. is by removing water.

4. A process for hydrocyanating 3-pentenenitrile in a reaction zone in the presence of a catalyst complex comprising a phosphorus-containing ligand and nickel metal, said process comprising:
    a. charging the catalyst complex, 3-pentenenitrile, a Lewis acid and HCN to the reaction zone;
    b. withdrawing reactor effluent comprising hydrocyanation product and catalyst complex from the reaction zone;
    c. contacting the reactor effluent with an extraction solvent to recover catalyst complex and remove impurities from the catalyst complex; and
    d. recharging at least a portion of the recovered catalyst complex to the reaction zone,
    wherein the amount of water in the catalyst complex recharged to the reaction zone in step d. is controlled to decrease the deactivation of the catalyst complex to less than about 5% compared to the process without said control.

5. The process of claim 4, wherein the amount of water is controlled by adding water.

6. The process of claim 4, wherein the amount of water is controlled by removing water.

7. The process of claim 4, wherein the phosphorus-containing ligand is a phosphorus-containing ligand of Structure I,

Structure I wherein in Structure I, $R^1$ and $R^2$ are the same or different, substituted or unsubstituted, monovalent aryl groups; $R^1$ and $R^2$ are bridged to one another or unbridged to one another; X is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, phosphitylbisaryl, phosphitylbisheteroaryl, hydroxybisaryl, hydroxybisheteroaryl, oxazole, amine, amide, nitrile, mercaptyl, and halogen groups.

8. The process of claim 7, wherein the phosphorus-containing ligand is a bidentate phosphorus-containing ligand having aromatic termini that are connected through a phosphorus-containing backbone linkage.

9. The process of claim 7, wherein the phosphorus-containing ligand is a bidentate phosphorus-containing ligand of Structure II,

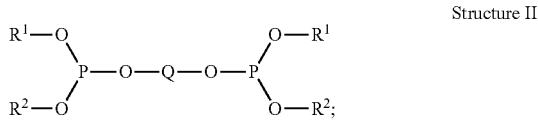

Structure II wherein in Structure II, O-Q-O is a divalent species of a bisaryl compound selected from the group consisting of Structure III, IV, or V, Structure III

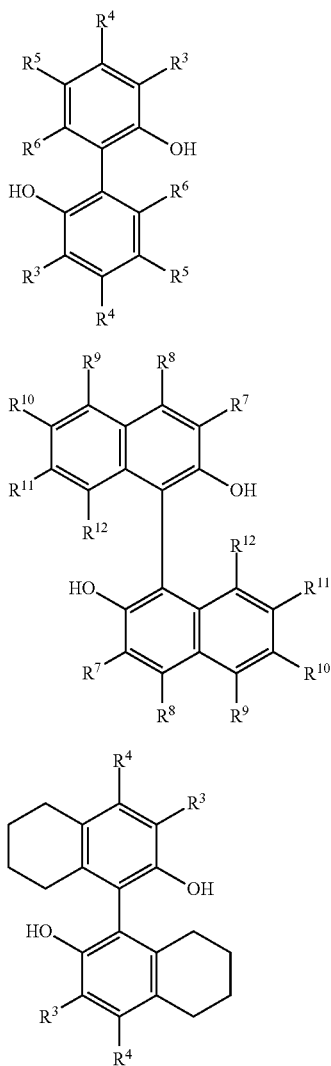

Structure IV

Structure V wherein in Structures II-V, $R^1$ and $R^2$ are the same or different, substituted or unsubstituted, monovalent aryl groups; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups.

10. The process of claim 7, wherein the phosphorus-containing ligand is a bidentate phosphorus-containing ligand of Structure VI, Structure VI

wherein $R^1$ and $R^2$ are the same or different, substituted or unsubstituted, monovalent aryl groups; each of $R^3$, $R^4$, $R^5$, $R^6$ is independently selected from the group consisting of hydrogen and $C_{1-10}$ alkyl.

11. The process of claim 7, wherein the phosphorus-containing ligand is a bidentate phosphorus-containing ligand of Structure VII, Structure VII

12. The process of claim 1, wherein the Lewis acid comprises zinc chloride or triphenylboron.

13. The process of claim 1, wherein processing downstream of the hydrocyanation reaction zone comprises a liquid-liquid extraction of the phosphorus-containing ligand from a dinitrile derived from the 3-pentenenitrile using a hydrocarbon extraction solvent.

14. The process of claim 1 wherein processing downstream of the hydrocyanation reaction zone comprises distillation.

15. The process of claim 1, wherein the amount of water is controlled so that the concentration of water in the reaction zone is about 100 ppm to about 300 ppm.

* * * * *